(12) United States Patent
Di Carlo et al.

(10) Patent No.: US 10,144,911 B2
(45) Date of Patent: Dec. 4, 2018

(54) METHOD AND DEVICE FOR SEPARATION OF PARTICLES AND CELLS USING GRADIENT MAGNETIC RATCHETING

(71) Applicant: THE REGENTS OF THE UNIVERSITY OF CALIFORNIA, Oakland, CA (US)

(72) Inventors: Dino Di Carlo, Los Angeles, CA (US); Coleman Murray, Los Angeles, CA (US); Edward Pao, Diamond Bar, CA (US); Peter Tseng, Saratoga, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 15/536,122

(22) PCT Filed: Dec. 15, 2015

(86) PCT No.: PCT/US2015/065624
§ 371 (c)(1),
(2) Date: Jun. 14, 2017

(87) PCT Pub. No.: WO2016/100234
PCT Pub. Date: Jun. 23, 2016

(65) Prior Publication Data
US 2017/0362563 A1   Dec. 21, 2017

Related U.S. Application Data

(60) Provisional application No. 62/262,294, filed on Dec. 2, 2015, provisional application No. 62/092,142, filed on Dec. 15, 2014.

(51) Int. Cl.
*B03C 1/00* (2006.01)
*C12M 1/00* (2006.01)
(Continued)

(52) U.S. Cl.
CPC ............... *C12M 47/04* (2013.01); *B03C 1/03* (2013.01); *B03C 1/0332* (2013.01); *B03C 1/247* (2013.01);
(Continued)

(58) Field of Classification Search
CPC ......... B03C 1/03; B03C 1/0332; B03C 1/247; B03C 1/253; B03C 1/588; C12M 47/04; G01N 15/0656
(Continued)

(56) References Cited

U.S. PATENT DOCUMENTS 4,324,577 A * 4/1982 Sepehri-Nik ........... C05B 13/02
                                                                 209/11
2004/0009614 A1   1/2004 Ahn et al.
(Continued)

OTHER PUBLICATIONS

PCT International Preliminary Report on Patentability (Chapter I of the Patent Cooperation Treaty) for PCT/US2015/065624, Applicant: The Regents of the University of California, Form PCT/IB/326 and 373, dated Jun. 29, 2017 (7pages).
(Continued)

*Primary Examiner* — Terrell H Matthews
(74) *Attorney, Agent, or Firm* — Vista IP Law Group LLP

(57) ABSTRACT

A system is provided for the quantitative magnetic separation of magnetic objects (e.g., particles or cells). The system uses magnetic ratcheting over arrays of ferromagnetic elements having gradient spacing manifested in various pitch zones that are encountered by the magnetic objects as they traverse the array. The system can be used to separate and concentrate magnetic objects based on iron oxide content. For cells, different phenotypes may be separated based, for example, on surface expression of proteins or molecules that are bound to magnetic particles. The system includes a substrate or chip having the array of ferromagnetic elements with increasing lateral pitch and an externally driven magnet
(Continued)

device that generates a cycling magnetic field. Magnetic objects with higher IOC separate and equilibrate along the array at larger pitches. The system can be used for the differential sorting of particles and cells of interest.

10 Claims, 15 Drawing Sheets

(51) Int. Cl.
    *B03C 1/03*     (2006.01)
    *G01N 15/06*     (2006.01)
    *B03C 1/033*     (2006.01)
    *B03C 1/247*     (2006.01)
    *B03C 1/253*     (2006.01)
    *B03C 1/28*     (2006.01)
    *G01N 35/00*     (2006.01)
    *G01N 15/00*     (2006.01)

(52) U.S. Cl.
    CPC .............. *B03C 1/253* (2013.01); *B03C 1/288* (2013.01); *G01N 15/0656* (2013.01); *G01N 35/0098* (2013.01); *B03C 2201/18* (2013.01); *B03C 2201/26* (2013.01); *G01N 2015/0053* (2013.01)

(58) Field of Classification Search
    USPC ...................................... 209/39, 40, 215, 216
    See application file for complete search history.

(56) References Cited

U.S. PATENT DOCUMENTS

| | | |
|---|---|---|
| 2005/0170418 A1 | 8/2005 | Moreland et al. |
| 2006/0020371 A1 | 1/2006 | Ham et al. |
| 2007/0215553 A1 | 9/2007 | Yellen et al. |
| 2008/0302732 A1 | 12/2008 | Soh et al. |
| 2009/0092509 A1 | 4/2009 | Barbic et al. |
| 2009/0159511 A1* | 6/2009 | Molteni ............... B03C 1/0335 209/636 |
| 2010/0078362 A1* | 4/2010 | Riise ........................ B03C 1/01 209/3.3 |
| 2010/0279887 A1 | 11/2010 | Lee et al. |
| 2011/0168618 A1* | 7/2011 | Danov ..................... B03C 1/18 210/222 |
| 2011/0212440 A1 | 9/2011 | Viovy et al. |
| 2012/0067787 A1 | 3/2012 | Riise et al. |
| 2013/0264248 A1* | 10/2013 | Smolkin .................. B03C 1/18 209/214 |
| 2014/0021105 A1 | 1/2014 | Lee et al. |

OTHER PUBLICATIONS

PCT International Search Report for PCT/US2015/065624, Applicant: The Regents of the University of California, Form PCT/ISA/210 and 220, dated Apr. 15, 2016 (3pages).
PCT Written Opinion of the International Search Authority for PCT/US2015/065624, Applicant: The Regents of the University of California, Form PCT/ISA/237, dated Apr. 15, 2016 (5pages).
Ahn, Chong H. et al., A Fully Integrated Micromachined Magnetic Particle Separator, J. Microelectromech. Syst. 1996, 5:151-158, 1996.
De Vries, Anthony H.B. et al., Micro Magnetic Tweezers for Nanomanipulation Inside Live Cells, Biophysical Journal 2005, 88:2137-2144.
Di Carlo, Dino et al., Dynamic Single Cell Culture Array, Lab on a Chip 2006, 6:1445-1449.
Do, Jaephil et al., Low-Cost Magnetic Interdigitated Array on a Plastic Wafer, IEEE Transactions on Magnetics 2004, vol. 40. No. 4, 3009-3011.
Dobson, Jon, Remote Control of Cellular Behaviour with Magnetic Nanoparticles, Nature Nano 2008, Mar., 139-143.
Gao, Jinhao et al., Intracellular Spatial Control of Fluorescent Magnetic Nanoparticles, JACS 2008, 130:3710-3711.
Lee, H. et al., Manipulation of Biological Cells Using a Microelectromagnetic Matrix, Appl. Phys. Lett. 2004, 35:1063-1065.
Mannix, Robert J. et al., Nanomagnetic Actuation of Receptor-Mediated Signal Transduction, Nature Nano Jan. 2008, 36-40.
Ramadan, Qasem et al., Microcoils for Transport of Magnetic Beads, Appl. Phys. Lett. 2006, 88:32501-1-3.
Thery, Manuel et al., The Extracellular Matrix Guides the Orientation of the Cell Division Axix, Nature Cell Biology 2005, 7:947-953; Supplementary Information, Nature Cell Biology, 2005, 1-4.
Zborowski, Maciej et al., Continuous Cell Separation Using Novel Magnetic Quadrupole Flow Sorter, Journal of Magnetism and Magnetic Materials, 194 (1999) 224-230.
Adams, Jonathan D. et al., Multitarget magnetic activated cell sorter, PNAS, Nov. 25, 2008, vol. 105, No. 47, 18165-18170.
Gao, Lu et al., The synchronization of superparamagnetic beads driven by a micro-magnetic ratchet, Lab Chip, 2010, 10, 2108-2114.
Gao, Lu et al., Multiplexing superparamagnetic beads driven by multi-frequency ratchets, Lab Chip, 2011, 11, 4214-4220.
Hiejazian, Majid et al., Lab on a chip for continuous-flow magnetic cell separation, Lab Chip, 2015, 15, 959-970.
Lim, Byeong et al., Magnetophoretic circuits for digital control of single particles and cells, Nature Communications, 5:3846; DOI: 10.1038/ncinns4846, www.nature.com/naturecommunications, 2014.
Lou, Xinhui et al., Micromagnetic selection of aptamers in microfluidic channels, PNAS, Mar. 3, 2009, vol. 106, No. 9, 2989-2994.
Pamme, Nicole et al., Continuous sorting of magnetic cells via on-chip free-flow magnetophoresis, Lab Chip, 2006, 6, 974-980.
Robert, Damien et al., Cell sorting by endocytotic capacity in a microfluidic magnetophoresis device, Lab Chip, 2011, 11, 1902-1910.
Tahir, Mukarram et al., Transport of superparamagnetic beads through a two-dimensional potential energy landscape, Physical Review E 84, 011403 (2011).
Tseng, Peter et al., Magnetic nanoparticle-mediated massively parallel mechanical modulation of single-cell behavior, Nature Methods, vol. 9, No. 11, Nov. 2012, 1113-1121.
Tseng, Peter et al., Flexible and Stretchable Micromagnet Arrays for Tunable Biointerfacing, Adv. Mater. 2015, 27, 1083-1089.
Tseng, Peter et al., Rapid and Dynamic Intracellular Patterning of Cell-Internalized Magnetic Fluorescent Nanoparticles, Nano Letters, 2009, vol. 9, No. 8, 3053-3059.
Yellen, Benjamin B. et al., Traveling wave magnetophoresis for high resolution chip based separations, Lab Chip, 2007, 7, 1681-1688.
Extended European search report dated Jul. 11, 2018 issued in European Patent Application No. 15870820.6-1203, (10pages).
Communication pursuant to Rules 70(2) and 70a(2) EPC dated Jul. 27, 2018 issued in European Patent Application No. 15870820.6-1203, (1page)

* cited by examiner

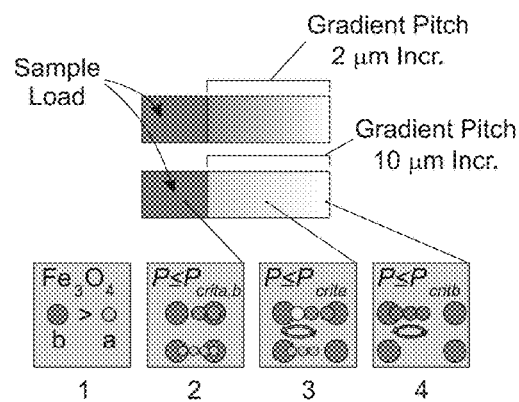
*FIG. 7*
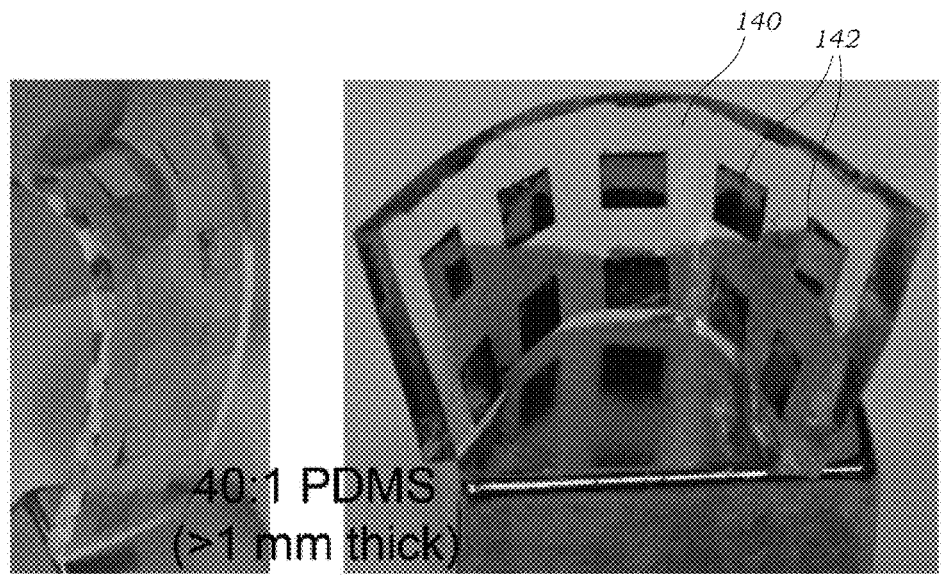
*FIG. 8A*   *FIG. 8B*

METHOD AND DEVICE FOR SEPARATION OF PARTICLES AND CELLS USING GRADIENT MAGNETIC RATCHETING

RELATED APPLICATIONS

This application is a U.S. National Stage filing under 35 U.S.C. § 371 of International Application No. PCT/US2015/065624, filed Dec. 14, 2015, which claims priority to U.S. Provisional Patent Application No. 62/092,142 filed on Dec. 15, 2014 and U.S. Provisional Patent Application No. 62/262,294 filed on Dec. 2, 2015. The contents of the aforementioned applications are hereby incorporated herein by reference in their entirely. Priority to the above-noted applications is hereby expressly claimed in accordance with 35 U.S.C. §§ 119, 120, 365 and 371 and any other applicable statutes.

STATEMENT REGARDING FEDERALLY SPONSORED RESEARCH AND DEVELOPMENT

This invention was made with Government support under OD007113, awarded by the National Institutes of Health. The Government has certain rights in the invention.

FIELD OF THE INVENTION

The field of the invention generally relates to methods and devices that use ferromagnetic elements embedded within or disposed on a surface; their uses; and methods of manufacture.

BACKGROUND OF THE INVENTION

Separating and concentrating cells from bulk solutions for analysis is a nontrivial task in life science research, diagnostics, and industrial processing. As such, various approaches based on physical or biochemical properties of cells have been developed to improve separation efficiency. Biochemical moieties on cell surfaces are most commonly used to distinguish cell populations, in which a specific receptor or protein is targeted with a recognition element (e.g., antibody, aptamer, ligand) to yield a fluorescent or magnetic label enabling downstream sorting.

The most widely used cell sorting techniques of this nature are fluorescence-activated cell sorting (FACS) and magnetic activated cell sorting (MACS). In FACS, multiple cell populations can be separated from heterogeneous mixtures based on the quantity of fluorophore associated with the cell. Though effective, the FACS process is performed serially and each cell is analyzed individually, increasing processing times for large sample volumes. Comparatively, magnetic based approaches are advantageous due to their simplicity and robustness, not requiring sophisticated fluid handling. These approaches are also able to operate on minimal cell quantities and/or process larger volumes more rapidly. However, magnetic separation approaches remain less quantitative than FACS, which can gate on the relative quantity of a biomarker. This lack of quantification from traditional MACS is due to the fact that these approaches cannot discriminate effectively based on the number of bound magnetic particles. Additionally, some magnetic particles available today are not tightly controlled in size or magnetic content, further exacerbating efforts for quantification of biomarker levels as correlated to number of bound particles, emphasizing the need for techniques to purify particles based on magnetic content.

Several microfluidics approaches have been developed to quantitatively separate cells based on bound or internalized magnetic content. In general, these techniques involve generating a magnetophoretic force orthogonal to a fluid flow direction, inducing cell deflection across streamlines and separation into different outlets depending on magnetic content. However, these "kinetic" based separations require precise tuning of flow rate, fluidic resistance, and magnetic field positioning. Additionally, many of these systems have low throughput as they rely on weaker bulk magnetic field gradients. Finally, the output from flow-through based systems often yields diluted solutions which may require additional concentration steps and is particularly challenging for isolating and locating rare cell types.

Magnetic ratcheting has the potential to achieve quantitative magnetic separations to both purify magnetic particle populations and separate cells based on bound number of particles. In magnetic ratcheting, arrays of magnetic micro-pillars combined with a directionally cycled magnetic field create dynamic potential energy wells that trap and manipulate magnetic particles in a magnetic-content and particle-size dependent manner. However, previous ratcheting platforms have utilized thin film magnetic structures (height≤200 nm), which have minimal force capacities on the order of 10 pN, due to the low aspect ratio of the structures used. To compensate, larger particles are used (~3-10 μm) to maximize the force envelope. However, larger particles have reduced magnetic labeling efficiency for cell separations due to slow diffusive motions. This slow diffusive motion results in inefficient binding of large particles to cell surface targets and the large increment in magnetic content per bound particle makes it difficult to relate bead binding to target expression levels. The use of smaller magnetic particles is necessary to increase labeling efficiency as well as provide a sensitive metric to relate bound particle numbers with cell surface expression, but is not practically compatible with current ratcheting technology. Additionally, previous ratcheting platforms rely on velocity differences between particles to achieve magnetic based separation. Again this is a "kinetic" separation requiring initial sample concentration prior to process initiation, and time dependent collection functions. These challenges have limited use as a quantitative sorting tool. Ideally, an equilibrium separation could achieve reduced dependence on initial and final conditions of a sample yielding a more robust and quantitative separation.

SUMMARY

In one aspect of the invention, a system is provided for the quantitative magnetic separation of magnetic objects such as particles and cells. The system uses high-force magnetic ratcheting over arrays of magnetically soft ferromagnetic elements in the form of micro-pillars having gradient spacing manifested in various pitch zones that are encountered by the particles or cells as they traverse the array. The system can be used to separate and concentrate magnetic beads or magnetically labeled cells based on iron oxide content (IOC). For cells, different cell types or phenotypes may be separated based, for example, on surface expression of proteins or molecules that are bound to magnetic particles. The system includes a substrate or chip having permalloy micro-pillar arrays with increasing lateral pitch and an externally driven magnet device that generates a cycling magnetic field. Particles (and cells) with higher IOC separate and equilibrate along the micro-pillar array at larger pitches. The differential sorting of particles and cells can be used to identify and extract particular particles or cells of interest.

In another embodiment, a system for the magnetic separation of magnetic objects includes a substrate and an array of ferromagnetic elements disposed on the substrate in rows and columns, wherein the array comprises a plurality of pitch zones having increased pitch between adjacent rows or columns of ferromagnetic elements. A support surface is disposed over the array of ferromagnetic elements and configured to receive the particles or cells. A rotating magnetic wheel is disposed adjacent to the support surface, the rotating magnetic wheel having disposed therein a plurality of permanent magnets arranged in a partial halbach array. Rotation of the magnetic wheel generates a cycling magnetic field that causes particles or cells that are located on the support surface to move in a ratcheting motion along the surface of the support surface and reach an equilibrium position based on the IOC of the cells or particles.

In another embodiment, a method for separating particles or cells includes binding magnetic particles to particles or cells and loading the particles or cells having the bound magnetic particles into a chip having an array of ferromagnetic elements disposed therein in rows and columns, wherein the array comprises a plurality of pitch zones having increasing pitch between adjacent rows or columns of ferromagnetic elements. A magnetic field is cycled adjacent to the chip, wherein cycling the magnetic field comprises or simulates rotating a plurality of permanent magnets arranged about an axis of rotation in a partial halbach array.

In another embodiment, a system for the separation of magnetic objects includes a chip device having an inlet, the inlet leading to a channel having an array of ferromagnetic elements disposed on a surface of the channel in rows and columns, wherein the array comprises a plurality of pitch zones having increased pitch between adjacent pitch zones. The system includes a ratcheting module holding a rotating magnetic wheel therein, the ratcheting module being disposed adjacent to the chip device, the rotating magnetic wheel having disposed therein a plurality of permanent magnets arranged in a partial halbach array.

In one embodiment, the ratcheting module is located in a housing (e.g., multi-part housing) and includes a first drive train coupling a first motor to the rotating magnetic wheel, wherein the rotation of the first motor causes rotation of the magnetic wheel. The ratcheting module also includes a second drive train having a second motor (e.g., stepper motor), whereby the second drive train is configured to twist the magnetic wheel in a plane substantially parallel to the chip device. The twisting motion may be accomplished by an interface formed between a gear located at the output or end of the second drive train and a rotatable ring (ring having circumferential surface with teeth that engage with output gear) that is secured to the first drive train and the first motor.

BRIEF DESCRIPTION OF THE DRAWINGS

FIG. 7 illustrates a photographic image of the ferromagnetic elements of FIGS. 6A and 6B disposed on a substrate. Located beneath the photographic image is a schematic illustration showing the movement of two different particles (a, b) with different sizes and/or magnetic strengths (b>a). Particles will traverse the array until reaching their critical pitch, $P_{crit\ a}$, $P_{crit\ b}$ (for each particle a, b) where they collect and oscillate with the cycling magnetic field. Particles with increasing magnetic content will have correspondingly higher critical pitches and therefore be separated.

FIGS. 8A and 8B illustrate two photographic images of an alternative embodiment that creates an array of ferromagnetic elements in a flexible substrate or surface.

DETAILED DESCRIPTION OF THE ILLUSTRATED EMBODIMENTS

Figure 1:
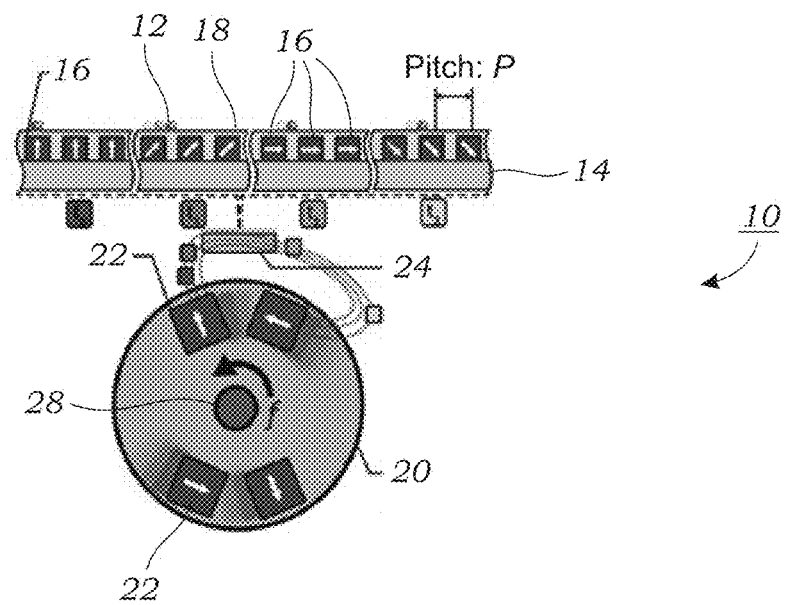
FIG. 1 illustrates a schematic representation of system that uses permalloy micro-pillars having pitch P to create dynamic potential energy wells which can be used to trap and manipulate particles or cells that have bound thereto magnetic particles. A rotating magnetic wheel is used to ratchet magnetic particles or cells across a surface.

FIG. 1 illustrates a system 10 for the magnetic separation of magnetic objects such as magnetic particles or cells 12 according to one embodiment. Magnetic objects include particles or the like that are naturally magnetic or, alternatively, particles that are non-magnetic that are then made to have magnetic properties. Magnetic objects also encompasses cells (live or dead) that have magnetic properties. Cells may be eukaryotic cells or cells may encompass bacteria. The system 10 includes a substrate 14 that has disposed thereon an array of ferromagnetic elements 16. A support surface 18 is disposed over the array of ferromagnetic elements 16 and configured to receive the magnetic particles or cells 12. As noted above, the particles 12 may naturally be magnetic or the particles 12 may be non-magnetic with magnetic particles bound or otherwise incorporated into the particle 12. Likewise, the cell 12 is non-magnetic but has magnetic particles that are bound, adhered, or otherwise incorporated within the cell 12 to provide the cell 12 with magnetic properties. The magnetic particles that bind to the cell 12 may be micrometer-sized or nanometer-sized particles (for example 5 micrometer in diameter, 1 micrometer in diameter, 500 nm in diameter, 100 nm or even down to 10 nm in diameter). Often, as explained herein, a cell 12 may have a number of magnetic particles bound to the cell which may be associated with a particular phenotype (e.g., cancer). As an increasing number of magnetic particles bind to the cell 12, this increases the magnetism of the cell 12. This property can be leveraged using the system described herein to preferentially separate and optionally analyze and/or collect these cells 12.

The system 10 includes a rotating magnetic wheel 20 that is disposed adjacent to the support surface 18 (either facing side or back side as illustrated). The rotating magnetic wheel 20 includes a plurality of permanent magnets 22 embedded or otherwise disposed therein and arranged in a partial halbach array as illustrated in FIG. 1. The rotating magnetic wheel 20, during rotation, generates a cycling magnetic field that generates the ratcheting movement of the particles or cells 12. In one aspect of the invention, the substrate 14 and support surface 18 are included as part of a larger chip 24 that includes a top or cover 26 (see FIGS. 4A-4D) that defines the inlets, outlets, flow channels or paths within the chip 24.

Still referring to FIG. 1, in one embodiment, the substrate 14 is formed from a stiff or rigid material such as glass. The array of ferromagnetic elements 16 is formed on the substrate 14 using, for example, electroplating of a nickel-iron alloy ($Ni_xFe_y$) within a photoresist mold or the like that is formed on the substrate 14. In one exemplary fabrication method, polished borosilicate glass is obtained and cleaned with piranha solution (30 min), washed in DI water and dried before deposition of a 50-nm-Ti, 200-nm-Cu and 50-nm-Ti seed layer (e.g., using E-beam evaporation). Next, a photoresist (e.g., SPR 220) is spun and processed according to specification to form electroplating molds for nickel-iron alloy. Ti is etched in 1% HF, and $Ni_xFe_y$ is electroplated to a ~4 µm thickness. The photoresist is stripped and both the Ti and Cu layers are etched completely. The chip is sealed by deposition of 100 nm silicon nitride SiN (PECVD). Spin-on polystyrene is spun to a thickness off ~1 µm above the pillars to form the support surface for the particles or cells to form the support surface 18. Before use, the substrate 14 is immersed in 2% by volume Pluronic F127 for 45 minutes. To create a fluidic chamber for the chip 24 (e.g., a full chip with a top and channels), PDMS (Dow-Corning) milli-channels were fabricated using scotch tape lithography and clamped (or bonded) to the substrate 14 containing the array of ferromagnetic elements 16. Solutions can be added to the chip 24 using a syringe or the like to add or inject fluid into a loading chamber or the like (e.g., using chamber or well 82 as seen in FIGS. 4A-4D).

As seen in FIG. 1, each ferromagnetic element 16 is formed as a permalloy micro-pillar having a circular cross-sectional shape although other shapes could be used. Each pillar that forms the ferromagnetic element 16 has an aspect ratio of about 1:1 (pillar height:pillar diameter). It should be appreciated, however, that ratcheting can still be successfully achieved even with extremely thin ferromagnetic elements 16 (e.g., aspect ratio ~10,000:1) using the in-plane ratcheting mode. The diameters of the pillars may vary depending on the application but the diameters generally fall within the range of 1 µm to 1000 µm. As explained below, when the array of ferromagnetic elements 16 are located adjacent to the rotating magnetic wheel 20, the ferromagnetic elements 16 or micro-pillars magnetize in alignment to the bulk magnetic field; modifying the magnetic potential energy landscape and introducing potential wells into which magnetic particles or cells 12 migrate. As the magnetic wheel 20 rotates, the magnetic particles or cells 12 follow the potential wells and ratchet through the ferromagnetic elements 16 based on their size and magnetic properties. Note that the particles or cells 12 migrate in a direction that is opposite to the rotation of the magnetic wheel 12. For example, as seen in FIG. 1, the magnetic wheel 20 rotates in the counter-clockwise direction and the particles or cells 12 move in the left-to-right direction.

As seen in FIG. 1, adjacent rows or columns (depending on the orientation) of ferromagnetic elements 16 are separated via a pitch distance, P. In one preferred aspect of the invention, the pitch distance P progressively increases in either the row direction or the column direction in certain separate pitch zones as discussed below. Each pitch zone is a sub-array of ferromagnetic elements 16 with the same pitch distance P within the sub-array (although with a greater pitch distance P than the immediately preceding pitch zone). The width of each pitch zone may vary but may be on the order of a few mm (e.g., 0.5 mm to 3 mm). For example, the pitch distance P between adjacent pitch zones of ferromagnetic elements 16 may increase in a linear fashion (e.g., 2 µm, 4 µm, 6 µm, 8 µm, etc.). In this last example, the pitch distance P increases in 2 µm increments. In other embodiments, the pitch distance in adjacent pitch zones could increase in an exponential or logarithmic fashion to increase the dynamic range of separation or achieve more refined separations respectively. In still other embodiments such as that illustrated in FIG. 6C, the pitch distance P may increase in both the column and row directions in different pitch zones. Within any one particular pitch zone, the pitch distance P does not increase until the next or adjacent pitch zone is reached. In an alternative construction of the device, however, the pitch zones may be omitted and the pitch distance P may increase with each adjacent column or row of ferromagnetic elements 16. For example, the incremental increase between each adjacent row and/or column could be very small, leading to a progressively increasing pitch rather than discrete pitch zones.

Still referring to FIG. 1, in one embodiment the rotating magnetic wheel 20 is a circular shaped disk that has embedded therein a plurality of permanent magnets 22 arranged in a partial halbach array. The diameter of the magnetic wheel 20 may vary but would typically fall within a range of about 0.5 inches to 6 inches. FIG. 1 illustrates four (4) N52 grade rare earth neodymium ferrite magnets (KJ Magnetics) arranged symmetrically within the magnetic wheel 20 with their respective poles pointed as indicated by the arrows of each permanent magnet 22. The strength of the permanent magnets 22 may vary. In experimental results described herein, the strength ranged from 20-200 mT. In alternative embodiments, more or less than four (4) permanent magnets 22 can be used. For example, there could be as many as eighty (80) permanent magnets 22 depending on the size of the magnetic wheel 20. Moreover, as noted below, in some embodiments, only a single rotating magnet may be used. Generally, the poles of the permanent magnets 22 alternate from being directed normal with respect to the axis of the array of ferromagnetic elements 16 to being directed tangential with respect to the axis of the array of ferromagnetic elements 16. The magnetic wheel 20 rotates about a rotational axis 28. The magnetic wheel 20 can rotate at a variety of rotational frequencies f. For example, the magnetic wheel 20 can rotate at frequencies between 0.0001 Hz and 100 Hz to create the ratcheting field although a range of about 1 to about 30 Hz is typically used. As explained herein, the rotational speed or frequency f may be automatically controlled as the rotating magnetic wheel 20 is mechanically coupled to an adjustable speed motor. FIG. 1 illustrates magnetic particles 12 of iron oxide ($Fe_3O_4$) that is being ratcheted across the support surface 18. Four (4) different time periods are shown, $t_0$, $t_1$, $t_2$, and $t_3$ with the magnetic particles 12 being ratcheted in the left to right direction.

Figure 5:
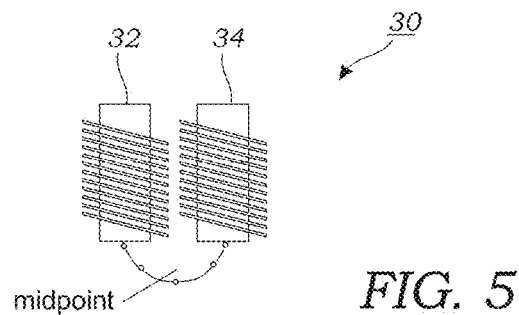
FIG. 5 illustrates an electromagnetic field generator that uses first and second electromagnetics instead of a physically rotating or spinning magnetic wheel.

FIG. 5 illustrates an alternative construction of an electromagnetic field generator 30 that uses first and second electromagnetics 32, 34 instead of a physically rotating or spinning magnetic wheel 20. This alternative embodiment uses an electromagnet to generate a cycling magnetic field. In yet another alternative, a single large spinning magnet rotating about an axis of rotation may be used as a substitute for the rotating magnetic wheel 20. For example, a square-shaped rare earth magnet having a side dimension within the range of about 0.25 inches to about 4 inches could be employed as an alternative. In yet another alternative construction a belt or tread having embedded permanent magnets 22 can be used as an alternative to the rotating magnetic wheel 20. In this embodiment, the belt or tread would be driven using a wheel, gear, or the like to provide the externally applied magnetic field.

Ratcheting transport is characterized by a balance of the time averaged magnetic force, $\overline{F_{mag}}$, with the time averaged drag force $\overline{F_{drag}}$ (see Eqs. 1 & 2 below). The time averaged magnetic force is dependent on several parameters including magnetic particle volume $V_p$, the particle susceptibility $\chi_p$, the permeability of free space $\mu_o$, and the magnetic flux density B.

$$\overline{F_{mag}} = \frac{V_p \chi_p}{\mu_o}(B \cdot \nabla)B \qquad \text{Eq. 1}$$

Assuming a Stokes drag condition, the time averaged drag force can be described in terms of fluid viscosity $\mu_f$, particle radius $r_p$, and the time averaged particle speed $\overline{u_p}$. The time averaged particle speed can be further represented in terms of the total distance traversed over one ratcheting cycle, $\overline{X_p}$, and the ratcheting frequency f (Eq. 2).

$$\overline{F_{drag}} = 6\pi\mu_f r_p \overline{u_p} = 6\pi\mu_f r_p \overline{X_p} f \qquad \text{Eq. 2}$$

Assuming the magnetic and drag forces equate, a particle ratcheted at a given frequency will be able to traverse a ratcheting array of pitch P given that $P \leq \overline{X_p}$ and the average particle velocity becomes Pf. However, when the pitch reaches a critical value $P = P_{crit} > \overline{X_p}$, the particle does not have sufficient migration time to reach the next pillar (and potential well) and will oscillate and become trapped (Eq. 3).

$$P_{crit} > \frac{V_p \chi_p}{\mu_o 6\pi\mu_f r_p} \frac{1}{f}(B \cdot \nabla)B \qquad \text{Eq. 3}$$

This bimodal behavior is dependent on driving frequency, horizontal pitch between ferromagnetic elements 16 (e.g., micro-pillars), particle size, and particle magnetic content. By designing an array of ferromagnetic elements 16 with a gradient in pitch in the row or column direction, particles or cells 12 with varying magnetic contents will equilibrate in different spatial locations and be separated from each other; as particles or cells 12 with higher magnetic content will have higher critical pitches. Furthermore, particles or cells 12 with similar magnetic content will concentrate into quantized bands at the critical pitch under a given driving frequency.

The net magnetic force on a magnetic particle or magnetically labeled cell 12 can be described as a summation of forces exerted by each bound particle $N_p$. The magnetic gradient, as well as magnetic force, decays strongly with inter-pillar distance and is concentrated locally near the magnetized ferromagnetic elements 16. This was quantified empirically by recording particle speeds across the chip 24 at various frequencies at each pitch and deriving the magnetic force. The magnetic force was best fit by a form $\alpha P^{-2}$, where $\alpha = 550$ pN$\mu$m$^2$ with $R^2 = 0.85$. Therefore the total magnetic force on a labeled cell 12 becomes $\overline{F_{mag}} = \alpha N_p P^{-2}$.

Equating the magnetic and drag forces on the cell and setting $P = P_{critcell}$, a relationship between the number of bound particles and the critical pitch can be derived (Eq. 4) where the cells critical pitch, $P_{critcell}$, relates to $N_p^{1/3}$.

$$P_{critcell} > \left[ N_p \frac{\alpha}{6\pi\mu_f r_{cell}} \frac{1}{f} \right]^{1/3} \qquad \text{Eq. 4}$$

Using Equation 4 as a predictive model, gradient ratcheting ferromagnetic arrays can be intelligently designed to achieve quantitative and highly resolved equilibrium magnetic separation of particles and cells 12.

Figure 2A:
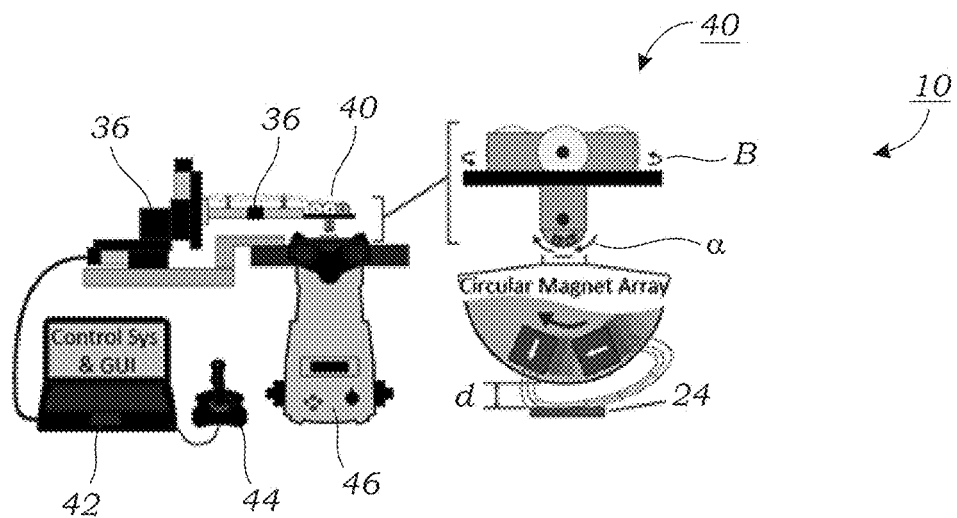
FIG. 2A illustrates an automated and microscope mounted ratcheting system that includes an XYZ positioning arm with a ratcheting module disposed at the end of the positioning arm. The ratcheting module provides for angular control of the ratcheting direction and ratcheting speed control. In this embodiment, the chip which holds the cells or particles is inverted. The inverted orientation was required for imaging using the microscope.

FIG. 2A illustrates an embodiment of an experimental system 10 used to perform magnetic ratcheting with particles and cells 12. In this embodiment, a xyz motion controller 36 is coupled to a ratcheting arm 38 that includes a ratcheting module 40 disposed at the end thereof. The xyz motion controller 36 imparts motion in the x, y, and z directions to place the ratcheting module 40 at the desired location adjacent to the substrate 14 or chip 24 as illustrated. The ratcheting module 40 provides two degrees of rotational motion to the magnetic wheel 20. First, the ratcheting module 40 drives rotation of the magnetic wheel 20 in the direction of arrows α. For example, the magnetic wheel 20 is mechanically geared or otherwise coupled to a motor to drive the rotation of the magnetic wheel 20. Rotation of the magnetic wheel 20 in the direction of arrows α provides the main ratcheting drive force for the particles or cells 12. The magnetic wheel 20 may also be rotated or "twisted" in the direction of arrows β (in the plane of the page of FIG. 2A). The twisting of the magnetic wheel 20 may also be automatically adjusted using the ratcheting module 40. As described herein, by enabling the magnetic wheel 20 to twist in this manner, ratcheting of particles or cells 12 can take place in two dimensions. The twisting of the magnetic wheel 20 followed by ratcheting in the perpendicular direction (or other direction) can be used to perform more refined separations (e.g., with a different frequency or pitch increment distance or functional form) or also be used to concentrate or extract certain sub-populations of particles or cells 12 that have been trapped at different locations along the array of ferromagnetic elements 16.

Still referring to FIG. 2A, the xyz motion controller 36 and the ratcheting module 40 are controlled by a control system 42 which may include a computer or the like as illustrated in FIG. 2A. The control system 42 is coupled to a manipulator 44 such as a joystick or the like that can be used to adjust the positioning of the xyz motion controller 36 and the ratcheting module 40 and control the rotation of the magnetic wheel 20. Alternatively, the control system 42 may be programmed with a preset program or set of instructions to position the magnetic wheel 20 adjacent to the chip 24 or substrate 14 and drive the magnetic wheel 20 in accordance with a predetermined order of operations (e.g., using MATLAB, LABVIEW or the like). For example, the program may orient the magnetic wheel 20 in a first orientation (e.g., positioned parallel to the rows or columns of ferromagnetic elements 16) and rotate at a frequency f for a set period of time, followed by a twisting of the magnetic wheel 20 (in the direction of arrows β, e.g., 90°), followed by another period of rotation of the magnetic wheel 20 at a frequency f for another set period of time. Note that rotation of the magnetic wheel 20 is typically stopped between twisting operations, however it can still rotate during the twisting operation. The sequence of movements and operations can be preloaded in the control system 42 and executed to run the separation routine. In some embodiments, the control system is also connected to an optical (e.g., microscopic) or electronic (e.g., impedance analysis) sensing system to identify the current state of the separation and feedback to the control system to modulate the frequency or direction of the cycling ratcheting field. For example, feedback may account for varying labeling efficiencies to adjust the rotation (or cycling) frequency and maximize the separation such that separated particles or cells are observed across the entire micro-pillar array.

In some embodiments, the xyz motion controller 36 may not be needed as the system may be designed to register the chip 24 or substrate 14 with respect to the ratcheting module 40 such that there is no need for robotic manipulation to move the ratcheting module 40 adjacent to the chip 24. For example, the chip 24 may be loaded into a tray or loading docket that is closed into position that places the chip 24 in close and uniform proximity to the ratcheting module 40.

As seen in FIG. 2A, the rotating magnetic wheel 20 is separated from the chip 24 by a distance d. This distance may be several mm (e.g., 2 mm) although other distances may be used depending on the strength of the permanent magnets 22. While FIG. 2A illustrates the magnetic wheel 20 disposed above the chip 24 it should be understood that the magnetic wheel 20 may be disposed beneath the chip 24 as well (as seen in FIG. 1). The rotating magnetic wheel 20 is located above the chip 24 in this configuration due to the presence of the microscope 46 that was used during experiments to image the particles and cells 12. In embodiments where there is no microscope 46, the magnetic wheel 20 is likely placed beneath the chip 24 as is seen in FIG. 1.

The size of the size of the rotating magnetic wheel 20 may vary. In some embodiments, the diameter of the magnetic wheel may be smaller than the chip 24 (i.e., a length of the array of ferromagnetic elements 16). In other embodiments, the diameter of the magnetic wheel may be larger than the chip 24. For example, the ratio of the diameter of the magnetic wheel 20 to the length of the chip 24 may vary from 1:10 to 10:1.

Figure 2B:
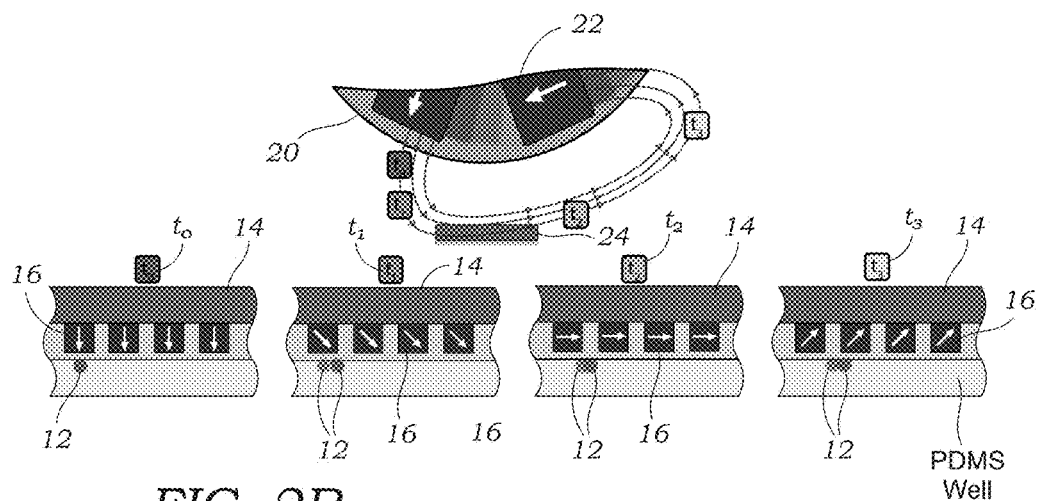
FIG. 2B illustrates the ratcheting movement of a magnetic particle in response to rotation of the rotating magnetic wheel.

FIG. 2B illustrates the arrangement of the chip 24 that was used in this "upside down" configuration for experimental testing. The chip 24 is first inverted onto a PDMS well containing aqueous buffer and is placed on the microscope 46. The ratcheting module 40 is positioned over the chip 24 with an offset of 2 mm. The system illustrated in FIG. 2A was able to operate at frequencies between 0.1 to 50 Hz. Note that the system was aligned to the ratcheting chips 24 such that the central axis of the ratcheting module 40 was aligned with the centroid of the ratcheting chip 24. While the system is preferably aligned to the centroid of the chip 24 the system will still function if there is some offset. Optimal results are obtained with alignment on the centroid region of the chip 24.

Figure 3:
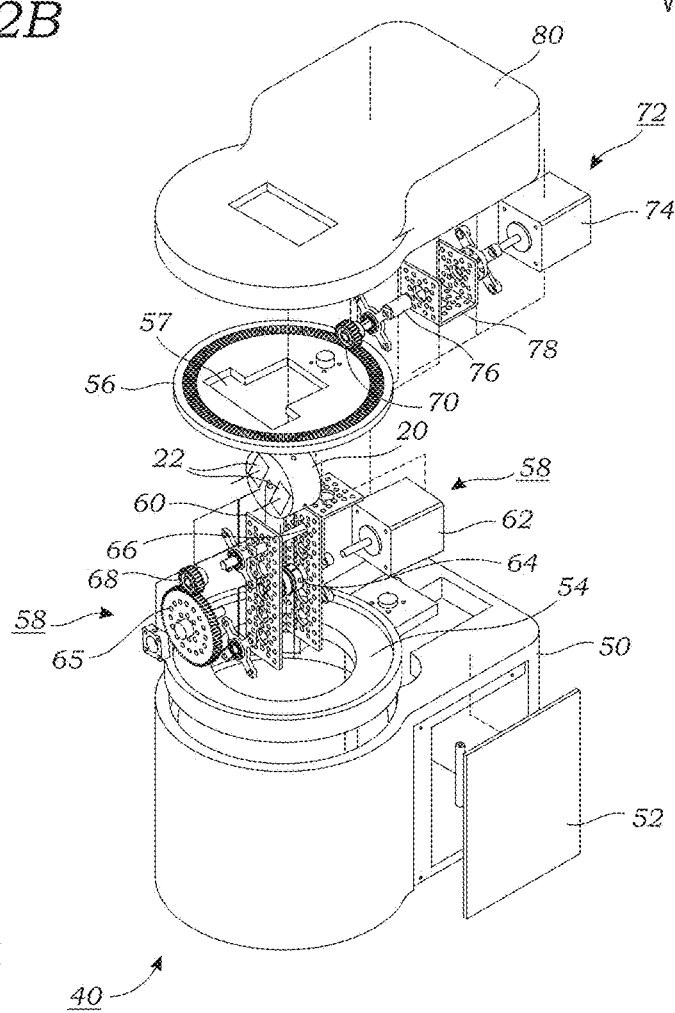
FIG. 3 illustrates a ratcheting module according to one embodiment.

FIG. 3 illustrates another embodiment of a ratcheting module 40. The ratcheting module 40 includes a base housing 50 that supports the ratcheting module 40 and provides an interior space for electronics (not shown) that can be accessed via access panel 52. The base housing 50 includes a support plate or rim 54 formed therein that holds a rotatable ring 56 disposed on the support plate 54 and rotatable relative thereto. The rotatable ring 56 includes an aperture 57 therein through which the magnetic wheel 20 partially passes. The rotatable ring 56 is secured to a drive train 58 via a frame 60 that operates to rotate the magnetic wheel 20. The drive train 58 includes first drive motor 62 that includes a flexible shaft coupling 64 (Flexible Shaft Coupling (McMaster Carr Standard Part 2764K122) that connects the shaft of the drive motor 62 to a gear 65 (e.g., 2.25 inch gear, Actobotics 615198). The magnetic wheel 20 is fixed to a shaft 66 that is mounted within the frame 60 and includes a gear 68 (0.75 inch gear, Actobotics 615250) at the end thereof that interfaces with the gear 65. The magnetic wheel 20 is able to twist by rotation of the rotatable ring 56. The rotatable ring 56 includes circumferential teeth that engage with a gear 70 (0.75 inch gear, Actobotics 615250) that is driven via a separate drive train 72. In this drive train 72, a stepper motor 74 (or DC motor) is used to drive a shaft 76 that extends through a frame 78 to directly drive the gear 70 which causes the rotatable ring 56 to rotate within the support plate or rim 54. This rotation of the rotatable ring 56 causes the magnetic wheel 20 to "twist" in the direction of (3 of FIG. 2A. The drive train 72 is contained in a top housing 80 which is secured to the base housing 50 to form the ratcheting module 40. Thus, in this embodiment, control of the speed of motor 62 controls the rotational speed or frequency f of the magnetic wheel 20. The stepper motor 74 is controlled to independently adjust the "twist" position of the magnetic wheel 20. Typically rotation of the magnetic wheel 20 is stopped between twisting operations and resumes once the desired twist rotation has been achieved although the magnetic wheel 20 could still spin or rotate during the twist operation.

In an alternative configuration, the magnetic wheel 20 may remain stationary while the chip 24 is able to twist in a plane that is substantially parallel to the chip 24. This produces the equivalent twisting motion albeit the chip 24 is twisted instead of the magnetic wheel 20. A similar ratcheting module 40 may be used to rotate the chip 24 relative to the stationary wheel 20. Of course, where reference is made to the stationary magnetic wheel 20, the magnetic wheel 20 is still able to rotate about its axis to provide the cycling magnetic field that produces the ratcheting motion of the particles or cells 12.

Figure 4A:
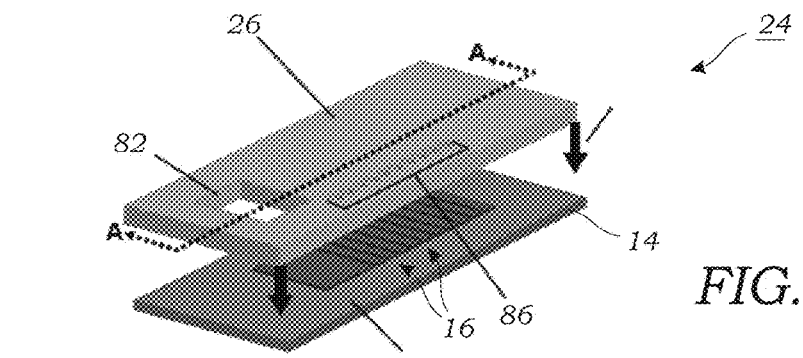
FIG. 4A illustrates a partially exploded view of a chip device according to one embodiment. The top is shown removed from the lower substrate that contains the array of ferromagnetic elements.
Figure 4B:
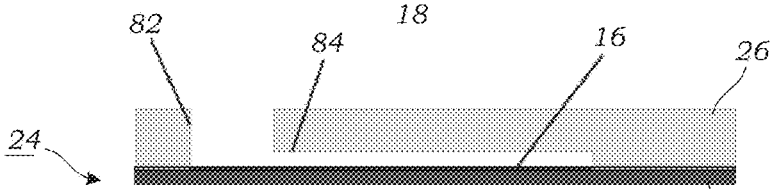
FIG. 4B illustrates a cross-section of the assembled device of FIG. 4A taken along line A-A of FIG. 4A.

FIGS. 4A-4B illustrate one embodiment of a chip 24. In this embodiment, the ferromagnetic elements 16 are located on a substrate 14 and are covered by a top or cover 26. The top or cover 26 may be clamped or permanently bonded to the substrate 14 containing the ferromagnetic elements 16. The cover 26 defines an input well 82 that leads to a channel 84 region that is defined as a space or gap (e.g., height between about 50-1,000 μm) that is formed between the support surface 18 that contains the particles or cells 12. A plurality of output wells 86 are formed in the cover 26 at locations near one end of the columns (or rows) of the ferromagnetic elements 16. Each column of ferromagnetic elements 16 with substantially uniform pitch has its own dedicated output well 86 to collect cells/particles a specific IOC. In this manner, particles or cells 12 that are trapped along a specific lateral position along the chip 24 (i.e., column or row) can be moved to the output well 86 by twisting the magnetic wheel 20 as explained in more detail below.

Figure 4C:
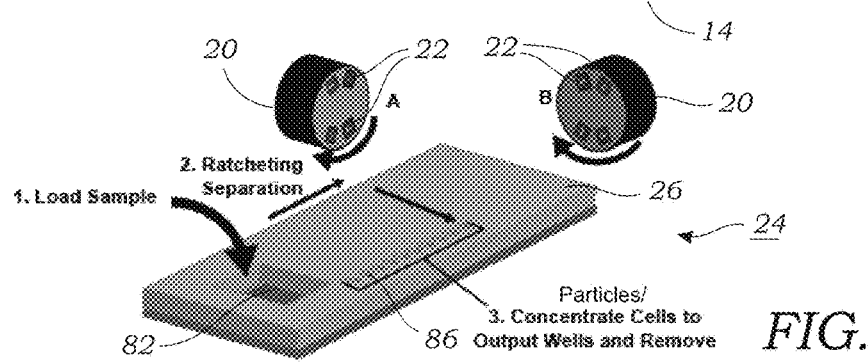
FIG. 4C illustrates a perspective view of the assembled device of FIG. 4B. Also illustrated is the sequence of operations used to separate the particles or cells. First, the sample is loaded into the input well. The particles or cells are then subject to ratcheting separation by rotation of the magnetic field in a first direction. The direction of the magnetic field is changed (still in same plane) and the particles or cells that have been separated in particular rows/columns of the array are then shunted to their corresponding outlet wells and removed from the chip.
Figure 4D:
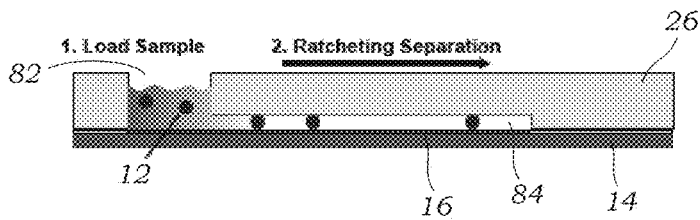
FIG. 4D illustrates a cross-sectional view of a sample being loaded into the chip device and undergoing ratcheting separation.

With reference to FIG. 4C, for a separation process using the chip 24 a sample containing the magnetically bound particles or cells 12 is loaded into the input well 82. A first ratcheting operation is performed with the magnetic wheel 20 oriented in orientation "A" so that ratcheting of particles or cells 12 occurs in the direction of the columns or rows of ferromagnetic elements 16 with increasing pitch distance. After the particles or cells 12 have reached their equilibrium positions the magnetic wheel 20 is then twisted to the orientation seen in orientation "B" (e.g., 90°) and then rotated again to move the particles or cells 12 to the corresponding output well 86 where they are concentrated. Movement can be achieved by using a lower frequency rotation such that all cells or particles can ratchet effectively for a designed pillar pitch in this second direction. The particles or cells 12 may be removed using standard microfluidic or macroscale techniques (e.g., negative pressure, pipetting, or the like) to obtain samples of solutions containing the concentrated particles or cells 12. Alternatively, imaging can be performed on this concentrated sample using fluorescence or brightfield field microscopic systems, a lensfree imaging system, or other sensing modalities. A concentrated area for imaging or sensing is advantageous as a smaller field of view requires less imaging time or allows for higher imaging resolution with the same time. An analysis can be output based on the total or relative number of cells/particles that equilibrate in each of these concentration regions, similar to a flow cytometry histogram of intensity of signal vs. cell quantity. It should be noted that if only an analysis is desired without collection the well structure 86 may be optionally excluded. One significant advantage over FACS is the ability to sort a cellular sample into many subpopulations corresponding to each output well 86 (e.g. eight (8) or twelve (12) or more), which is challenging to achieve with FACS. In one embodiment, the well 86 uses a linear spacing and size that matches that of a standard 96-well or 384-well plate to allow integration with multi-well pipettors and robotic liquid handler systems.

Figure 6A:
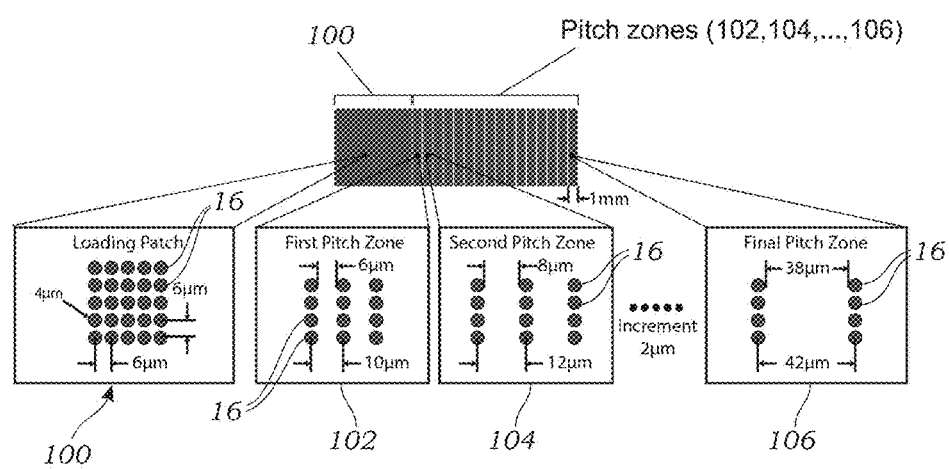
FIG. 6A illustrates an array of ferromagnetic elements arranged on a substrate or chip with an increasing pitch (in the row direction) in the amount of 2 µm. The initial loading patch (with uniform pitch in the row and column directions) is illustrated along with the first, second, and final pitch zone.

A variety of sample types may be used in connection with the system described herein. For example, the sample that is loaded into chip 24 may include blood, urine, or other body fluids such as pleural effusions, peritoneal effusions, cerebral fluids, amniotic fluid, sperm-containing fluids, tears, tissue digests, cell cultures, and the like, FIG. 6A illustrates one embodiment of an array of ferromagnetic elements 16. In this embodiment, there is a collection or loading patch 100 that includes rows and columns of individual ferromagnetic elements 16 with a uniform pitch. In this example, all of the ferromagnetic elements 16 have a diameter of 4 μm although other dimensions may be used. In the collection or loading patch 100, there is a 6 μm gap between adjacent ferromagnetic elements 16 but again other pitch dimensions may be used. The overall size of the collection or loading patch 100 is 1 cm×1 cm. In this embodiment, the columns of ferromagnetic elements 16 are divided into a series of pitch zones with each adjacent pitch zone having an increasing pitch increment of 2 μm. Each individual pitch zone has a dimension of 1 cm×1 mm. The first pitch zone 102 located adjacent to the collection or loading patch 100 includes a pitch of 10 μm between adjacent ferromagnetic elements 16 in the horizontal (i.e., row) direction. In a second pitch zone 104 located adjacent to the first pitch zone 102 includes a pitch of 12 μm between adjacent ferromagnetic elements 16 in the horizontal (i.e., row) direction. In a final pitch zone 106 located at the end of the array of ferromagnetic elements 16 includes a pitch of 42 μm between adjacent ferromagnetic elements 16 in the horizontal (i.e., row) direction. The total length of the ferromagnetic elements 16 including the first pitch zone 102 and the final pitch zone 106 is 1.7 cm.

Figure 6B:
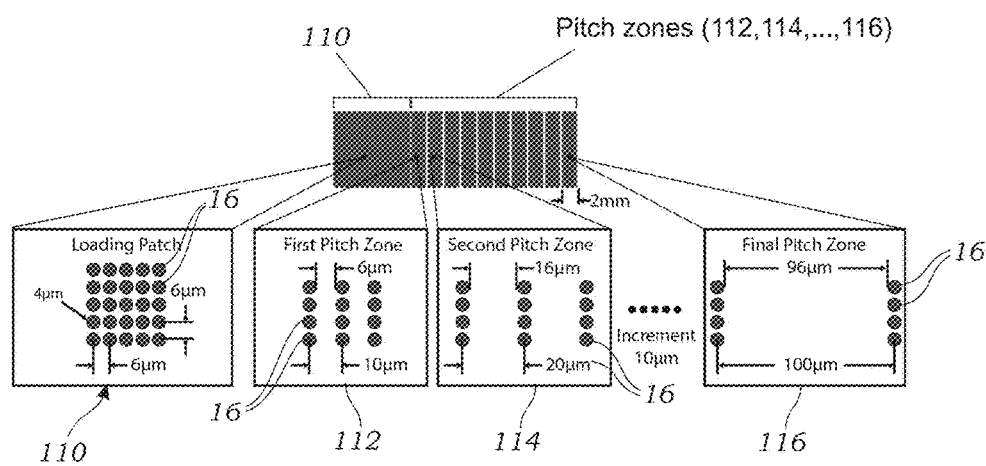
FIG. 6B illustrates an array of ferromagnetic elements arranged on a substrate or chip with an increasing pitch (in the row direction) in the amount of 10 µm. The initial loading patch (with uniform pitch in the row and column directions) is illustrated along with the first, second, and final pitch zone.

FIG. 6B illustrates another embodiment of an array of ferromagnetic elements 16. In this embodiment, there is a collection or loading patch 110 that includes rows and columns of individual ferromagnetic elements 16 with a uniform pitch. In this example, all of the ferromagnetic elements 16 have a diameter of 4 μm although other dimensions may be used. In the collection or loading patch 110, there is a 6 μm pitch between adjacent ferromagnetic elements 16 although other pitch sizes could be employed. The overall size of the collection or loading patch 110 is 1 cm×1 cm. In this embodiment, the columns of ferromagnetic elements 16 are divided into a series of pitch zones with each adjacent pitch zone having an increasing pitch increment of 10 μm. Each individual pitch zone has a dimension of 1 cm×2 mm. In a first pitch zone 112 located adjacent to the collection or loading patch 100 includes a pitch of 10 μm between adjacent ferromagnetic elements 16 in the horizontal (i.e., row) direction. In a second pitch zone 114 located adjacent to the first pitch zone 112 includes a pitch of 20 μm between adjacent ferromagnetic elements 16 in the horizontal (i.e., row) direction. In a final pitch zone 116 located at the end of the array of ferromagnetic elements 16 includes a pitch of 100 μm between adjacent ferromagnetic elements 16 in the horizontal (i.e., row) direction. The total length of the ferromagnetic elements 16 including the first pitch zone 102 and the final pitch zone 106 is 2 cm.

Figure 6C:
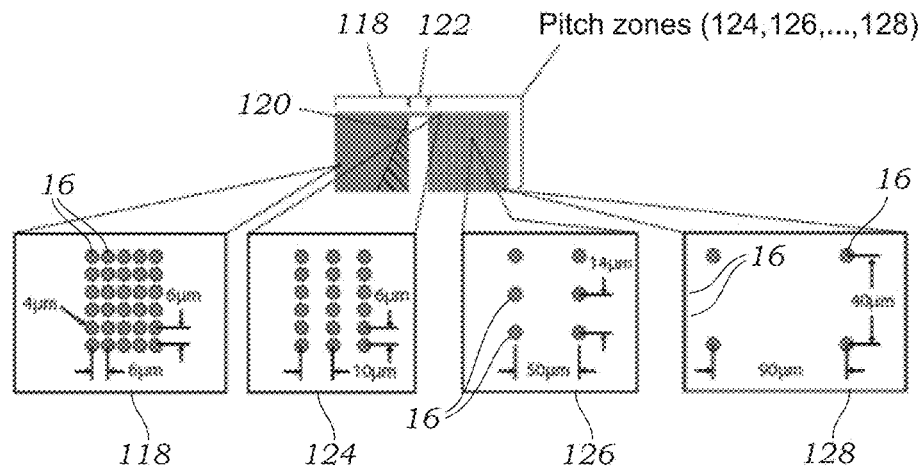
FIG. 6C illustrates another embodiment of an array of ferromagnetic elements arranged on a substrate or chip that includes increasing pitch in both the row direction and the column direction.

FIG. 6C illustrates another embodiment of array of ferromagnetic elements 16. In this embodiment, there is a collection or loading patch 118 that includes rows and columns of individual ferromagnetic elements 16 with a uniform pitch. In this example, all of the ferromagnetic elements 16 have a diameter of 4 μm although other dimensions may be used. In the collection or loading patch 118, there is a 6 μm pitch between adjacent ferromagnetic elements 16 but other pitch dimensions could be employed. The overall size of the collection or loading patch 118 is 1 cm×1 cm. The collection patch 118 includes a non-magnetic funnel 120 which may include a wall or side of the chip 24 that is angled and necks down to a corner or narrow portion of the loading patch 118. The funnel 120 is used to channel or herd the particles or cells 12 to a bridge array 122. A bridge array 122 containing ferromagnetic elements 16 (with uniform pitch spacing of 6 μm) connects the collection or loading patch 118 to another series of pitch zones 124, 126, 128. As seen in FIG. 6C, the columns of ferromagnetic elements 16 are divided into a series of pitch zones with each adjacent pitch zone 124, 126, 128 having an increasing pitch increment of 10 μm in the horizontal (i.e., row) direction and an increasing pitch increment of 2 μm in the vertical (i.e., column) direction. In a first pitch zone 124 located adjacent to the collection or loading patch 118 includes a pitch of 10 μm between adjacent ferromagnetic elements 16 in the horizontal (i.e., row) direction and a pitch of 6 μm between adjacent ferromagnetic elements 16 in the vertical (i.e., column) direction. In a second pitch zone 126 (which is not adjacent to the first pitch zone 124 and is located downstream therefrom separated by intervening pitch zones) includes a pitch of 50 μm between adjacent ferromagnetic elements 16 in the horizontal (i.e., row) direction and a pitch of 14 μm between adjacent ferromagnetic elements 16 in the vertical (i.e., column) direction. In a final pitch zone 128 located at the end of the array of ferromagnetic elements 16 includes a pitch of 90 μm between adjacent ferromagnetic elements 16 in the horizontal (i.e., row) direction and a pitch of 40 μm between adjacent ferromagnetic elements 16 in the vertical (i.e., column) direction.

The embodiment of FIG. 6C can be used to perform two-dimensional separation of the particles or cells 12. For example, all particles are aligned in the "vertical" direction using the bridge array 122. A first separation can be performed by ratcheting the particles or cells 12 in the horizontal direction (i.e., row direction). After the first separation is performed, the rotating magnet 20 (or other external magnet source) can be twisted to change the orientation of the rotating magnet 20 through an angle of 90°. The rotating magnet 20 can then be spun or rotated to perform another separation of the particles or cells 12 in an orthogonal direction. The second separation is a more fine-tuned separation due to the smaller pitch distance. Alternatively, rather than having two separate ratcheting operations at orthogonal orientations of the rotating magnet 20, the rotating magnet 20 could be oriented at an angle to the columns/rows of ferromagnetic elements 16 (e.g., 45°) to perform separations in both directions simultaneously. In still another alternative, the pitch in one direction may increase geometrically or exponentially while the pitch in the other direction may increase in a linear fashion.

Figure 6D:
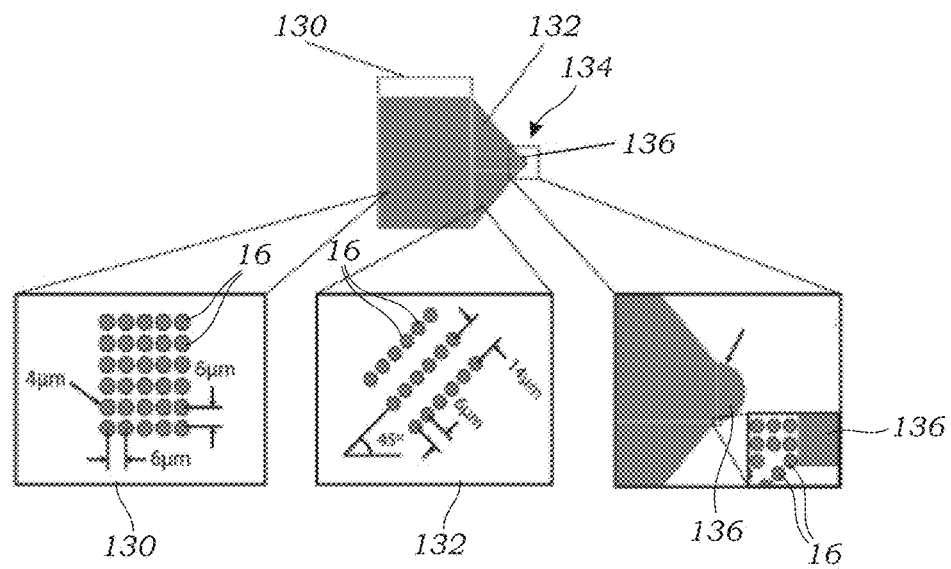
FIG. 6D illustrates another embodiment of an array of ferromagnetic elements arranged on a substrate or chip that includes slanted or angled arrays of ferromagnetic elements that end in a concentration area or patch.

FIG. 6D illustrates another embodiment of array of ferromagnetic elements 16. In this embodiment, there is a collection or loading patch 130 that includes rows and columns of individual ferromagnetic elements 16 with a uniform pitch. In this example, all of the ferromagnetic elements 16 have a diameter of 4 μm although other dimensions may be used. In the collection or loading patch 130, there is a 6 μm pitch between adjacent ferromagnetic elements 16 although other pitch distances may be used. The overall size of the collection or loading patch 130 is 2.5 cm×1.5 cm. Located adjacent to the collection or loading patch 130 is an array 132 of ferromagnetic elements 16 that is angled or tilted relative to the orientation of the collection or loading patch 130. The array 132 of ferromagnetic elements also is triangular in shape that terminates in an apex 134 or end that is located at the farthest point away from the collection or loading patch 130. For example, in the illustrated embodiment, the columns or rows of the array 132 are angled 45° with respect to the columns or rows of the collection or loading patch 130 (other angles may be used). A concentration region or patch 136 formed at or near the apex 134 to collect the particles or cells 12. For example, the patch 136 may have a semicircular shape with a diameter of 500 μm although other geometries and sizes may be used.

In the embodiment of FIG. 6D, after particles or cells 12 collected on the collection or loading patch 130, the particle or cells 12 are ratcheted toward the right of the chip 24. Upon ratcheting from the left to right, the magnetically labelled particles or cells 12 travel across the loading patch 130 and funnel down to the angled array 132 and progress to the concentration patch 136. The concentration patch 136 is a single permalloy structure and is not composed of individual separate ferromagnetic elements. The targeted particles and cells 12 become trapped at the concentration patch 136 for final collection. Alternatively, the trapped particles and cells 12 may be imaged in the small area of the concentration patch 136.

In various alternative embodiments, different pitch increments and angles for the array 132 array could be used. For example pitches between 5-50 μm with a distance between angled lanes >2× of the pitch within a lane, and angles between about 10° to about 70° can be used. Note that different pitches or frequencies of ratcheting can be used to perform selective concentration in the concentration patch of the most magnetic particles for example or cells 12 with the most attached beads.

FIG. 7 illustrates a photographic image of the ferromagnetic elements of FIGS. 6A and 6B disposed on a substrate. Located beneath the photographic image is a schematic illustration showing the movement of two different iron oxide particles (a, b) with different sizes and/or magnetic strengths (b>a). Particles will traverse the array until reaching their critical pitch, $P_{crit}$, where they collect and oscillate (illustrated by ovals). Particles with increasing magnetic content will have correspondingly higher critical pitches and therefore be separated. As seen in the panel schematic #2 the pitch P is less than $P_{crit}$ for both particle a and particle b with both particles a and b being able to ratchet to the next ferromagnetic element 16 (e.g., micro-pillar). In panel schematic #3 the pitch P is less than $P_{crit}$ for particle b yet the pitch P is greater than $P_{crit}$ for particle a. Hence, particle a cannot move to the adjacent micro-pillar while particle b is able to ratchet to the next micro-pillar. In panel schematic #4, the pitch P is greater than $P_{crit}$ for particle b (of course also larger for particle a). Thus, particle b cannot make the jump to the next micro-pillar.

In an alternative embodiment, as seen in FIGS. 8A and 8B, instead of forming the substrate 14 from glass, the substrate 140 may be formed from a flexible material that contains ferromagnetic elements 142 embedded therein. In this embodiment, magnetic material is electroplated within elastomeric materials to form flexible magnetic hybrid materials. The flexible structures are fabricated via direct micromachining on thin films with tunable solubility (rendered only soluble in water with monovalent ions, such as salt) to micromachine robust films of permalloy (nickel iron alloy), which are subsequently sacrificed and surface patterned on polydimethylsiloxane (PDMS) of varying elastic moduli (below 100 kPa), although other elastomeric curable polymers could also be used. In particular, the manufacturing method uses poly-acrylic acid thin films for the micromachining of the ferromagnetic material. Poly-acrylic acid films can be rendered insoluble in water via soaking in $CaCl_2$, which crosslinks the network to form insoluble $Ca^{2+}$-PAA. This film is stable in the presence of high concentrations of bivalent ions, which can include $Ni^{2+}$ and $Fe^{2+}$, in addition to $Ca^{2+}$. This film can subsequently reacquire water solubility via the introduction of monovalent ions, such as Nat After $Ca^{2+}$-PAA layer deposition, the surface is treated with air plasma and evaporated a seed layer of Ti—Cu—Ti to form the base of the electroplated magnetic material. Micro-magnets can generally be patterned using either positive or negative photoresists.

To ensure proper bonding to PDMS, a thin layer of titanium (30 nm) was sputtered and silanized to yield allyl functionality for direct cross-linking with PDMS. This direct bonding of metals to PDMS avoids silicon dioxide intermediate layers, which are highly brittle and crack under minimal strain. $Ca^{2+}$-PAA layers were typically etched in NaCl-water over 24 hours on a shaker. Larger chips (>2.5 cm) can take longer to sacrifice, and this process can be accelerated using gentle plying of the PDMS with tweezers. FIGS. 8A and 8B illustrate images of relatively thick (>1 mm), soft PDMS structure (40:1 PDMS) that bend under magnetic stimuli.

Figure 9:
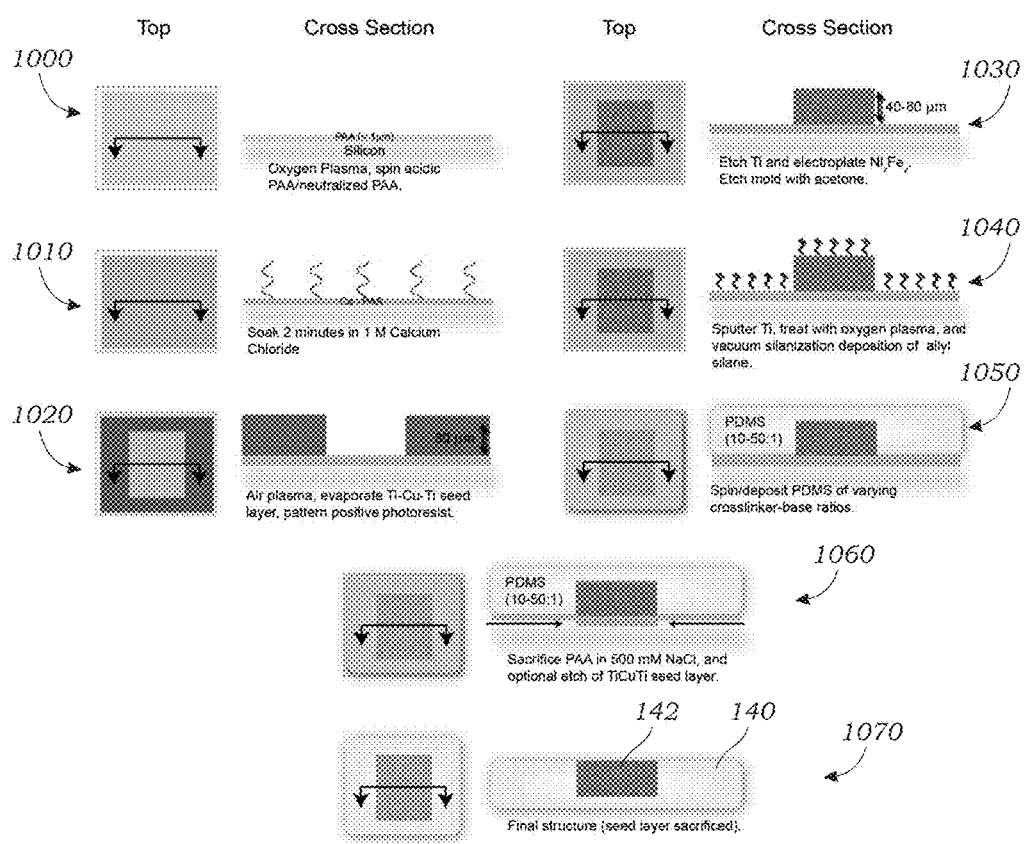
FIG. 9 illustrates an exemplary method of forming a flexible substrate or surface that incorporates ferromagnetic elements therein.

FIG. 9 illustrates a method used to create a flexible substrate 140 that contains ferromagnetic elements 142 embedded therein. As seen in operation 1000, <100> silicon wafers were cleaned with acetone, methanol, and isopropanol, before treatment with oxygen plasma. Poly-acrylic acid thin films were generated using methods demonstrated by Linder, et al., V. Linder, B. D. Gates, D. Ryan, B. A. Parviz, G. M. Whitesides, Small Weinh. Bergstr. Ger. 2005, 1, 730, which is incorporated by reference herein. Poly-acrylic acid solution (100 kDa, Sigma) at 2% w/v was spun at 3000 rpm onto silicon wafers, and allowed to react with the surface at 150 degrees C. over 1 hour to form a partially insoluble thin film of PAA. This acts as an adhesion layer for $Ca^{2+}$-PAA. PAA neutralized with sodium hydroxide (at 6% w/v) was then spun onto silicon wafers, and allowed to dry at 150 degrees over 3 minutes.

As seen in operation 1010, substrates were subsequently soaked in 1 M $CaCl_2$ over 1 minute (e.g., 2 minutes), gently washed in DI water, and dried over pressurized air. With reference to operation 1020, substrates were treated for 5 seconds in air plasma (Harrick), before a Ti (30 nm)-Cu (200 nm)-Ti (30 nm) seed layer was deposited. A SPR220 resist can be used, spun to thicknesses up to 70 µm as the electroplating mold. Due to the high absorbance of the photoresist, multiple exposure—development cycles were used to properly develop the seed layer for thicker resist layers. With reference to operation 1030, permalloy was electroplated using a nickel and iron sulfate-based bath. A variety of permalloy thicknesses (2 µm to 70 µm) and sizes (4 µm to 5 mm) can be deposited. Upon electroplating completion, samples were washed with 100 mM $CaCl_2$, and the photoresist was directly etched in acetone. With reference to operation 1040, a 30-nm-thick layer of titanium was then sputtered onto samples. Wafers were treated in oxygen plasma (40 W, 10 seconds), and silanized with allyl trimethoxy silane (Sigma). As seen in operation 1050, PDMS of varying elastic moduli was finally spun or poured onto substrates, and allowed to cure at room temperature over at least 24 hours, and then cured at 60 degrees overnight. Still referring to FIG. 9, in operation 1060 substrates were released in either phosphate-buffered saline or saline solution (200 mM) over 24 hours on a shaker. Larger substrates/magnetic structures (>2 cm) were encouraged via gentle plying of the metal seed layer to expedite this process. Seed layers were etched with 1% HF (for titanium) and 5% Acetic Acid, 15% $H_2O_2$ (for copper). Operation 1070 illustrates the final, liberated structure. Samples as processed were generally stable to repeated tagging and usage, however samples were typically wiped with a thin layer of PDMS (<2 µm, generated by successive wipes by a glass slide) onto these substrates to ensure long-term stability.

A variety of substrates 140 with varying thicknesses and sizes can be constructed with varied elastic properties. Thin PDMS membranes can be folded, while metal structures on 40:1 PDMS can be morphed or stretched in x- and y-dimensions. The permalloy elements 142 retain initial size, and remain crack-free despite significant deformation of the PDMS. These flexible substrates 140 handle differentially, and manipulate uniquely under magnetic field stimuli. Due to the large size and volume of deposited material, chips could be manipulated readily nearby a magnet. In general, a thick, stiffer PDMS structure is used to interface with flat substrates such as slides while thinner membranes of PDMS are used for wrapping around tubes (e.g., Eppendorf tubes), and ultra-flexible layers for experiments that require complex warping of the magnetic structures. Magnetic-PDMS with moduli ~100 kPa were highly stable under stretch approaching 200% and more of initial size. Structures did not crack, and retained their initial positions upon relaxation under these conditions. In one embodiment a flexible array of ferromagnetic pillars is generated with a single pitch and is stretched to achieve a desired pitch for each experiment or application. In this way only a single fabrication mask or process flow can be used to create structures with different pitches, allowing for better economies of scale. In a related embodiment, the flexible array is stretched non-uniformly (e.g., in a single direction to create a gradient in pitches, or in two separate directions to create a 2D array with separate pitches in separate directions).

The trapping effect of the flexible substrates 140 with permalloy elements 142 were utilized to contour the flow path of magnetic particles in microfluidic channels by morphing soft magnetic-PDMS elements flanking the bottom of coverslip-mounted microfluidic channels. Particles can also be trapped around the permalloy elements 142, and subsequently released by removing the flexible film and producing lower incident fields. Released particles flowed along pathways delineated by the reconfigurable morphed micromagnet array. The substrates 140 can be used to pattern magnetic structures within flat and along curved surfaces using magnetic matrices of 500 µm or 1 mm squares. Flexible substrates 140 can be used to pattern magnetic particles (Spherotech, 4.4 µm) within Eppendorf tubes, and within fluidic droplets under relatively low incident magnetic fields (20 mT). These particles could be readily micromanipulated within these structures by reorienting the magnetic elements in relation to the permanent magnet.

The flexible properties of the substrates 140 can be used to confer tunable, additive capabilities to magnetic droplet manipulation. First, the addition of the flexible micromagnet-containing substrate 140 protects the arrayed particles against large scale manipulation of the main permanent magnet, allowing selective manipulation of magnetic droplets. Second, by selectively removing particles from their associated local micro-magnet, particles were then free to either be extracted from the droplet, or to manipulate the droplet itself. This allows the generation of two additional droplet behaviors: 1) sub-selection of particles for controlled extraction, and 2) formation of bipolar magnetic droplets, possessing both leading and trailing edges of magnetic particles within a single droplet. Extraction of specific subpopulations of particles from droplets could potentially allow for sequential time-dependent analysis of chemical environments within a droplet (e.g., cytokine production from captured immune cells).

The ultra-soft layers of magnetic-PDMS substrates 140 could form a dynamic yet simple, reusable interface to pattern biological structures on standard coverslips used in biological labs. Magnetizable cells were generated by dosing HeLa cells with magnetic nanoparticles, and subsequently seeded these onto a single coverslip flanked by two magnetic matrices of 500 µm elements integrated into soft PDMS (40:1). One matrix was left in a native conformation, while the second was morphed in both x- and y-dimensions to form a strained structure. The low elasticity of the PDMS allowed the morphed structure to remain structurally stable purely due to non-covalent stiction of the PDMS to the glass coverslip. Upon application of a permanent magnet, cells manipulated into cell aggregates, shaped by the local magnetic field generated by the micro-magnets. Interestingly, several hours after adhering, these aggregates exhibit characteristics similar to tissues patterned via surface patterning, such as larger internal populations of cells and the parallel elongation of cells along the tissue edge. In addition, tuning the orientation of the magnet with the external field yielded uniquely polarized 2D tissues. These structures possessed some 3D characteristics, as large, local fields force cells to grow above each other. The size of these individual micro-tissues correlated well with respective cell counts, and micro-tissues at the edge of the magnetic matrix generally had higher cell counts in comparison to those in the interior. A comparison of the orientation of generated micro-tissues in unstrained versus morphed matrices demonstrated the spread of tissue orientation as a result of the morphed structure. Structures oriented broadly over 80 degrees over morphed patterns, in comparison to 10 degree spread over unstrained features. Micro-tissues formed by morphed structures also possessed unique shapes as a result of complex angular interactions between the incident field and the ferromagnetic elements 142.

Using the substrates 140 with ferromagnetic elements 142 embedded therein a versatile method is disclosed of integrating high quality permalloy features of varying size (4 µm to 5 mm) and thickness (1 µm to 70 µm) into PDMS of varying elastic properties (10:1 to 50:1) using poly-acrylic acid thin films. The versatility of this process enables one to generate various unique, additive behaviors in commonly used substrates in a biology laboratory. Different forms of magnetic-PDMS co-structures could integrate seamlessly alongside coverslips, Eppendorf tubes, and fluidic channels to micro-manipulate particles and form biostructures; this may potentially generate new applications in magnetic droplet control, magnetophoresis, bio-patterning, and self-assembly. These structures could potentially integrate alongside biological structures, such as the epidermis or blood vessel, and, for example, be utilized alongside antigen-scavenging magnetic particles.

Figures 10A, 10B:
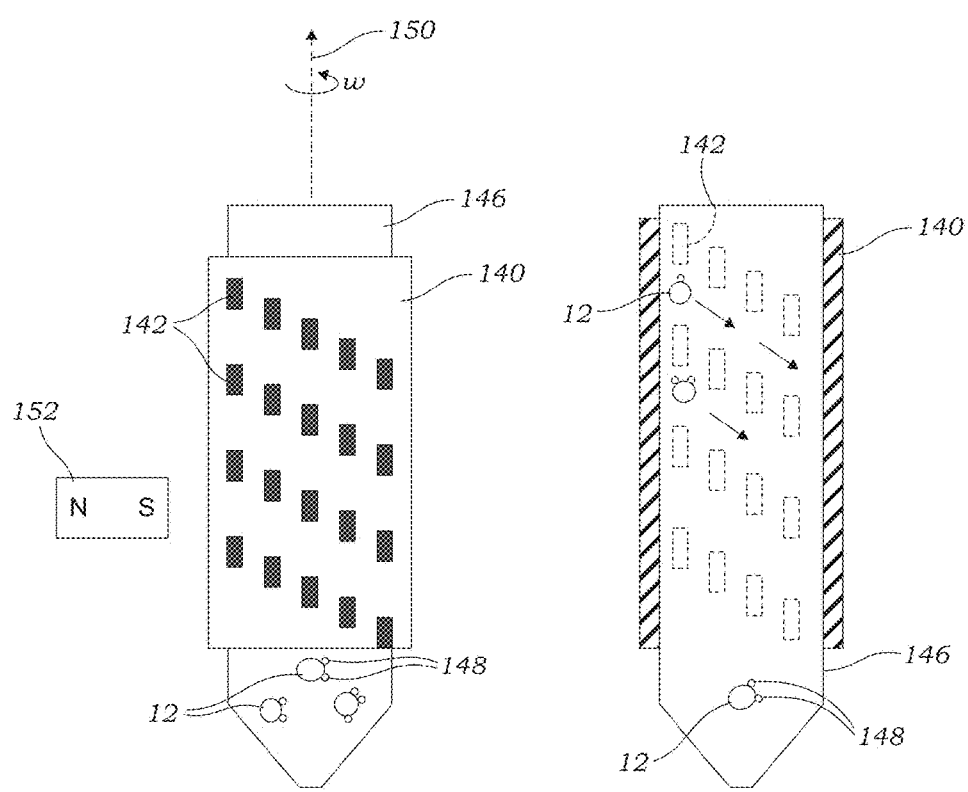
FIG. 10A illustrates a tube (e.g., rigid tube made of plastic or glass) that is wrapped with a jacket that is made from a flexible substrate or surface that incorporates ferromagnetic elements. A permanent magnet is illustrated adjacent to the tube. The tube rotates an axis of rotation to concentrate magnetically labelled cells or particles at the bottom of the tube.
FIG. 10B illustrates a cross-sectional view of the tube wrapped in the flexible jacket. Cells labelled with magnetic particles are shown ratcheting along the inner surface of the tube towards the bottom of the tube.

FIGS. 10A and 10B illustrates one particular application of a flexible substrate 140 containing ferromagnetic elements 142 embedded therein. In this embodiment, as seen in FIG. 10A, the flexible substrate 140 with the ferromagnetic elements 142 is wrapped around a tube 146 (e.g., Eppendorf tube) as a flexible jacket or the like. The tube 146 contains a solution containing particles or cells 12 that are labelled with magnetic particles 148 as described herein. For example, the magnetic particles 148 may bind to a particular expressed protein or molecule that is presented on the exterior surface of the cell 12. The cell 12 may have a number of magnetic particles 148 that are bound to the individual cell 12. The tube 146 is rotated about an axis of rotation 150 that extends down the central axis of the tube 146. For example, the tube 146 may be held in a receptacle or holder that is able to spin the tube 146 about the axis of rotation 150. The tube 146 and flexible substrate 140 or jacket also rotates with the tube. A permanent magnet 152 is positioned adjacent to the tube 146 and jacket.

FIG. 10B illustrates an inner surface of the tube 146. During rotation of the tube 146 the cells 12 containing the bound particles 148 move in a ratcheting movement around and down to the end of the tube 146 (in direction of arrow of FIG. 10B). The rotational speed ω at which the tube 146 rotates may be adjusted to isolate cells 12 with different numbers of particles 148 bound thereto. In addition, the flexible substrate 140 may be designed with ferromagnetic elements 142 with a varied pitch along the longitudinal length of the tube 146.

Figure 11:
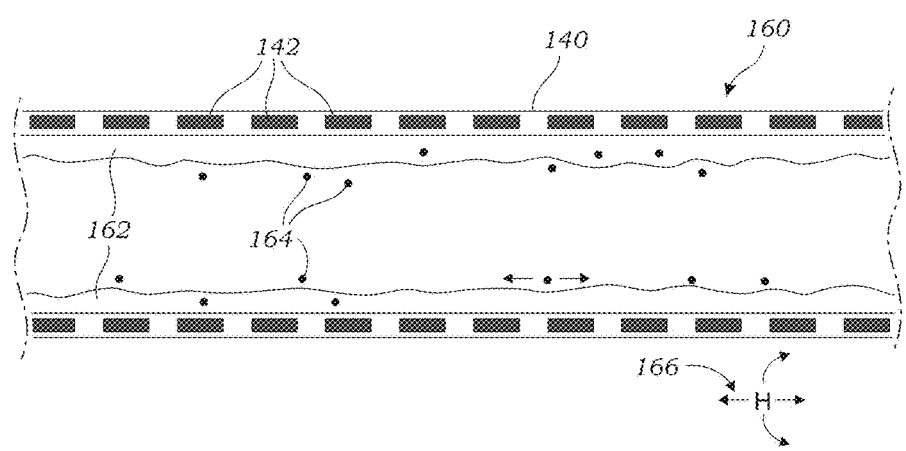
FIG. 11 illustrates a flexible tube such as a catheter that is made from the flexible substrate or surface that incorporates ferromagnetic elements. Magnetic particles are flowed in the tube and manipulated by an externally applied magnetic field to disrupt a biofilm or other biomaterial that is formed on an inner luminal surface of the tube.

FIG. 11 illustrates still another application of the flexible substrate 140 containing ferromagnetic elements 142 embedded therein. FIG. 11 illustrates a cross-sectional view of a flexible tube 160 that carries fluid therein. The flexible tube 160 may include, for example, a catheter or the like. In this embodiment, the ferromagnetic elements 142 are circumferentially positioned around the flexible tube 160. The inner luminal surface of the flexible tube 160 is illustrated as containing a biofilm 162 that is adhering to the flexible tube 160. For example, after extended use of catheters, biological material often tends to build-up and form on the inner surface which may cause clogging of the catheter or can lead to a source of contamination and infection. In this embodiment, magnetic particles 164 are flushed through the flexible tube 160 and a moving, external magnetic field 166 is applied to move the magnetic particles 164 back-and-forth inside the flexible tube 160 (see arrows in FIG. 11). The moving magnetic field 166 may be applied by a moving permanent magnetic, a rotating permanent magnet, or an electromagnet which can either be located on the side of the flexible tube 160 or circumferentially about the tube 160. The back-and-forth motion may include motion along the longitudinal length of the flexible tube 160 or circumferential motion or some combination of the two. The movement of magnetic particles 164 mechanically disrupts the biofilm or other biomaterial that adheres to the inner luminal surface of the flexible tube 160.

Experimental

Experiments were conducted using the rigid, glass substrate 14 as described herein with an array of ferromagnetic elements 16 disposed thereon. To characterize the system separation behavior of the device, magnetic particles 12 with varying diameters and iron oxide (IO) content were separated under several driving frequencies. Magnetic particles of 2.8 µm, 4.6 µm and 5 µm were made fluorescent through a variety of surface modifications for imaging using the microscope 46 of FIG. 2A. Particle concentrations ranged between $0.5 \sim 1 \times 10^6$ particles/mL. Particle separation was observed by inverting the chip 24 onto a PDMS milli-channel which was placed on the stage of a Nikon Eclipse Ti fluorescent microscope 46 and positioning the ratcheting module 40 above it. The particles were injected onto the ratcheting chip loading patch, ratcheted at various frequencies, and imaged under 10× objective using the DAPI, FITC and TRITC filter sets. Image analysis with ImageJ was used to identify particle distributions.

Particles ratcheted at a given frequency will traverse an array as long as the pitch, P, remains at or below that particle's critical pitch value, $P_{crit}$. In this regime the particle displays a linear relationship between particle speed and frequency. The particle will traverse the array until $P > P_{crit}$ where it is unable to traverse to the next micro-pillar and will equilibrate and concentrate at the edge of this pitch region.

Figure 12A:
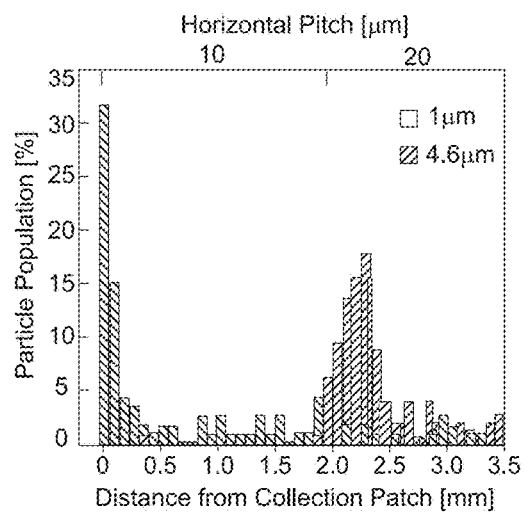
FIG. 12A illustrates a graph showing the results of separation of a mixture of 1 µm and 4.6 µm fluorescent particles on a chip having 10 µm incremented ferromagnetic elements. Particle population (%) is illustrated as a function of distance from the collection patch (mm).
Figure 12B:
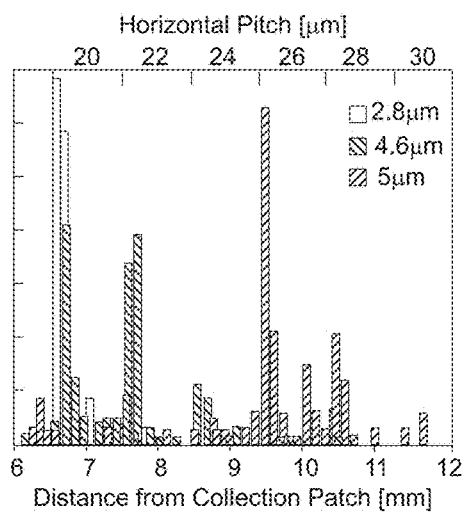
FIG. 12B illustrates a graph showing the results of separation of a mixture of 2.8 µm, 4.6 µm, and 5 µm fluorescent particles on a chip having 10 µm incremented ferromagnetic elements. Particle population (%) is illustrated as a function of distance from the collection patch (mm).

Successful separation of mixed 1 µm and 4.6 µm particles was achieved using a 10 µm incremented chip at 30 Hz achieving ≥90% purity and 9 pg of IO resolution as seen in FIG. 12A. Though small, some inter-population overlap was observed which is suspected due to 1 µm particle aggregates or a lack of quality control in particle size. In addition to separation, each particle population was concentrated by 500 fold from bulk solution. As expected, the 2 µm incremented chip leads to finer resolved separations with a mixture of three particle types demonstrating a resolution of 5.6 pg of IO as seen in FIG. 12B. The 2.8 µm particles could be easily separated from 5 µm particles with a >90% purity. Interestingly, the 4.6 µm particles subdivided into three subpopulations at the 20, 22 and 24 µm pitches which was unexpected as the model predicted a critical pitch of 24 µm for this particle. It was determined that this behavior was most likely due to variations in IO content as derived from the particle data sheet. This suggests that the system can achieve resolutions bordering on 1 pg of IO. However, these findings also demonstrate that the system is highly sensitive to variability in particle manufacturing which could be a potential limitation if the iron oxide content varies significantly between particles. To address this challenge, another potential application for the system is as a quality control or manufacturing tool for analyzing IO content of a batch of particles or enriching particles with similar iron oxide content or assessing the distribution of IO content within a sample. Using this mode, it was found that 1 µm particles were highly homogenous in iron oxide content where >90% of the injected particle population equilibrated at a single critical pitch.

After characterizing separation behavior, the magnetic ratcheting separation system was used to measure and concentrate cell populations based on surface expression level of Epithelial Cell Adhesion Molecule (EpCAM) using the 1 µm particles. It was found that the quantity of 1 µm diameter, anti-EpCAM magnetic particle binding correlated with αEpCAM immunofluorescence on two prostate cancer lines with differential expression. LNCaP cells have been reported to have high but varying EpCAM expression (337, 000±37% molecules/cell), which was in agreement with additional flow cytometry analysis that demonstrated a variation from mean fluorescence of ±27%. PC3 cells have comparatively lower EpCAM expression levels, ~52,000±78% molecules/cell which was confirmed with flow cytometry analysis. The quantity of bound magnetic particles followed a similar trend where PC3 cells ranged between 1-41 bound particles per cell while a majority of LNCaPs ranged between 21-103 particles per cell ($N_{LNCaP}$=508, $N_{PC3}$=57, p=5.7e-6).

After it was confirmed that particle binding correlated positively with EpCAM expression, LNCaP cells were magnetically labeled and separated using the ratcheting system. Cells were injected at 50 µL/min via a syringe/PEEK tube assembly onto the ratcheting chip's loading patch. Note that chips with both 2 µm and 10 µm pitch increments where characterized. Simultaneously the ratcheting module was positioned over the loading patch to concentrate the cells. 1 µm iron oxide particles (Invitrogen) with anti-EpCAM (abcam) were diluted with PBS+0.5% BSA to a concentration of $10^6$ particles/mL and added to a solution of fixed LNCaP or PC3 cells (4% paraformaldehyde) at a 1:100 cell to particle ratio. Labeling was performed at room temperature with gentle mixing for at least 1 hour. Anti-mouse IgG Alexa Fluor-488 secondary (Invitrogen) was added to stain and visualize the particles and cell nuclei labeled with Hoesch. Therefore, both cells and particles could be visualized and imaged fluorescently for analysis. The solution was then washed and resuspended into 1 mL of PBS. The quantity of particles per cell was determined using florescent image analysis (entire chip imaged under DAPI and FITC wavelengths), where the bound particle intensity was summed over the cell and normalized to the nuclear area. This metric was in turn used to determine PPC values. Stitched images of ratcheted cells and particles were analyzed using an automated MATLAB script to crop each cell, sum the intensity value of the particles (FITC), and normalize to the total cell area (DAPI). This numerical value was proportional to the number of bound particles per cell and was calibrated for each image analyzed to determine the PPC value. A calibration curve between the cell area normalized particle intensity value and particles per cell (counted manually in Image J) was generated to quantify the number of bound particles.

Figure 13A:
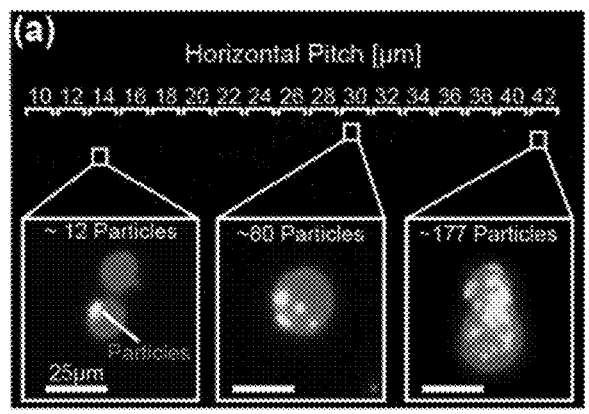
FIG. 13A illustrates a stitched image of magnetically labeled LNCaP cells equilibrating at different pitches within a 2 µm incremented chip driven at 5 Hz frequency. Insets show cells equilibrating at pitches according to quantity of particles per cell (PPC).
Figures 13B, 13C:
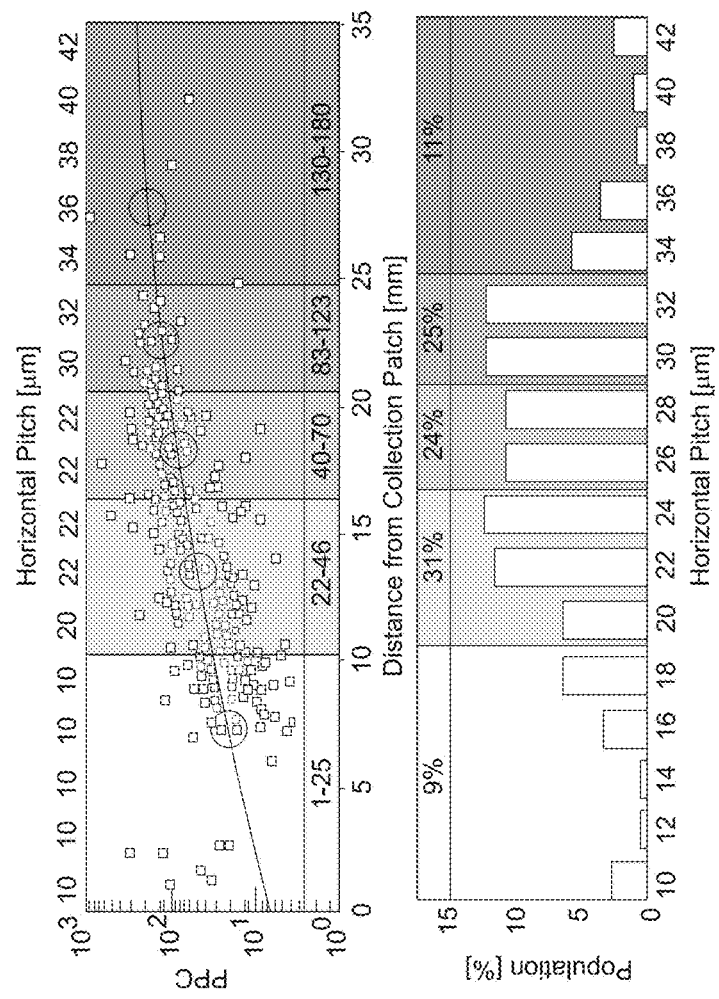
FIG. 13B illustrates a graph that plots the PPC versus the on-chip location and critical pitch of individual cells (points) for a 2 µm incremented chip driven at 5 Hz frequency. The theoretical ⅓ power relationship between PPC and pitch is shown as a solid line. Five statistically significant ($p<0.05$) populations were identified ranging from 1-25, 22-46, 40-70, 83-123 & 130-180 particles per cell with corresponding averages (black circles). Each subpopulation equilibrated at increasing horizontal pitches, correlating well with the theoretical model ($R^2=0.91$).
FIG. 13C illustrates the cell distribution as a function of pitch for a 2 µm incremented chip driven at 5 Hz frequency (N=508).
Figure 14A:
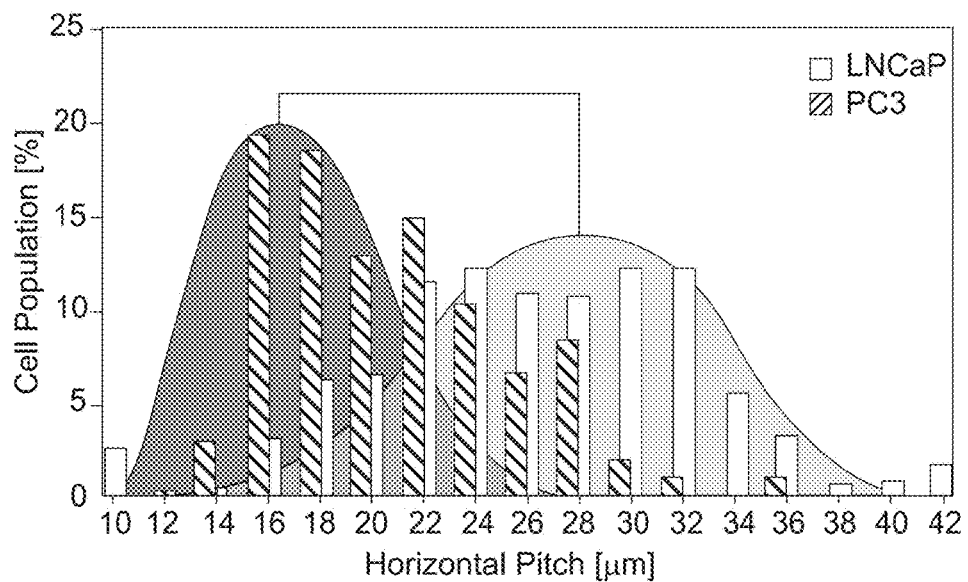
FIG. 14A illustrates a graph illustrating the differential population distributions of PC3 and LNCaP cells that were separated using a 2 µm incremented chip ratcheted at 5 Hz.
Figure 14B:
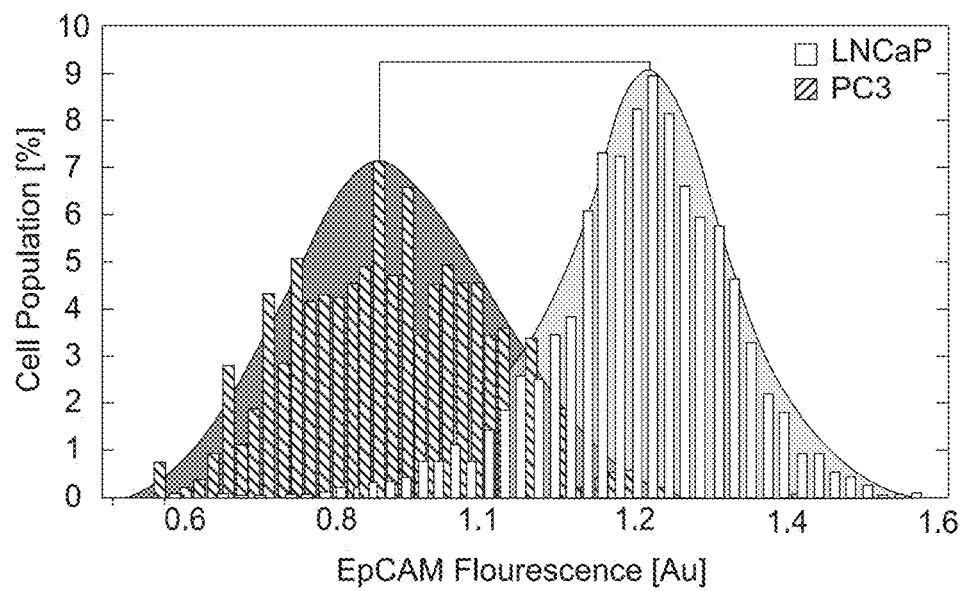
FIG. 14B illustrate flow cytometry results for a similar mixture of PC3 and LNCaP cells showing a similar trend in the differential expression of PC3 and LNCaP cell populations.

Labeled LNCaPs driven with a 5 Hz ratchet for about 10 minutes separated and equilibrated at critical pitches according to their bound particle quantity as seen in FIGS. 13A and 13B. Using kmeans statistical analysis, cells were binned (unpaired two-tailed t-test, p<<0.05) into five subpopulations (FIG. 13B) with particle binding quantities of 1-25, 22-46, 40-70, 83-123 &130-180 particles per cell (PPC) each equilibrating at their corresponding critical pitches. The average PPC's for each subpopulation demonstrated the expected ⅓ power relationship between critical pitch and PPC, in agreement with the predictive (Equation 4, $R^2$=0.91). Furthermore, the system was able to resolve the cells at high resolution resolving a 13 particle differential between the 10-24 µm pitch regions. Additionally, the population distribution from the ratcheting cytometry chip (FIG. 13C) was similar to flow cytometry data on the same LNCaP population (FIGS. 14A and 14B). The LNCaP distribution was centered on the 22 µm pitch and had a coefficient of variation of 37%, which was close to the flow cytometry distribution with a 27% coefficient of variation.

Figures 13D, 13E:
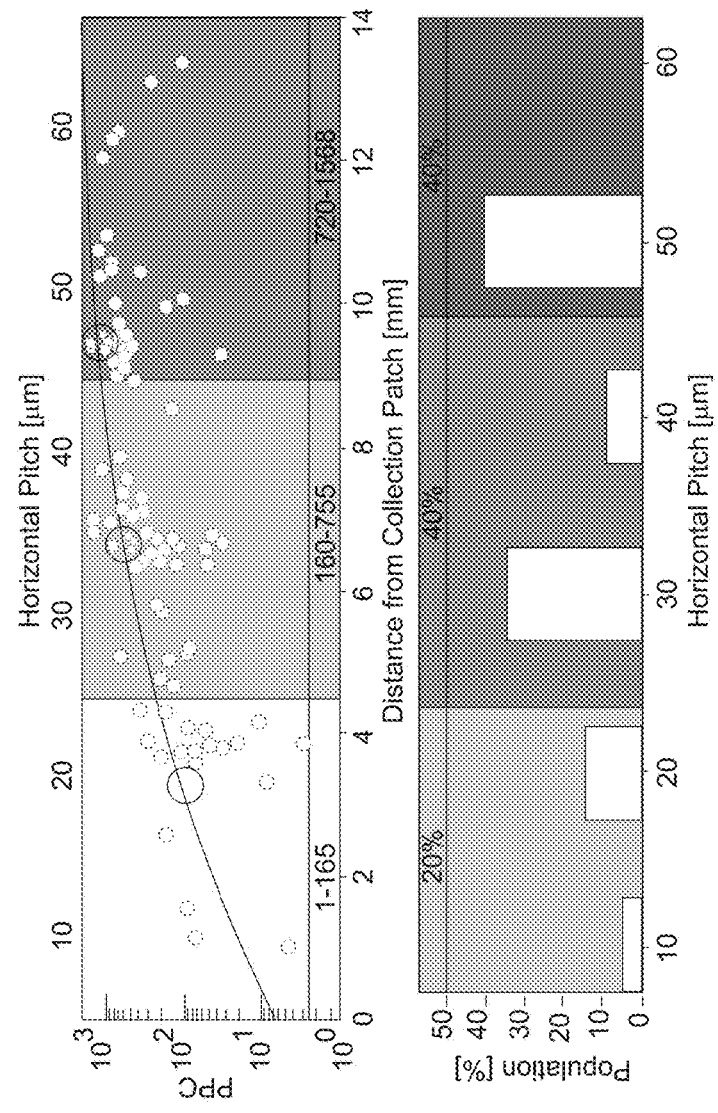
FIG. 13D illustrates the PPC distribution of magnetically labeled LNCaP cells for a 10 µm incremented chip at 5 Hz, again correlating with the predicted model ($R^2=0.89$). More punctuate trapping is observed due to the coarseness of the pitch gradient and additional populations of more strongly labeled cells are observed compared to the 2 µm incremented chip.
FIG. 13E illustrates the cell distribution as a function of pitch for a 10 µm incremented chip driven at 5 Hz frequency

To accommodate separation and enrichment of cells with larger magnetic signatures, ratcheting cytometry with labeled LNCaPs was also performed on a 10 µm incremented chip driven at 5 Hz (FIGS. 13E and 13E). Using the same kmeans and t-test analysis, three PPC ranges of 1-165, 160-755 and 720-1598 PPC were resolved. This behavior on the 10 µm incremented chip also correlated with the predictive model ($R^2$=0.89) and separated a subpopulation of cells that was not detected in the 2 µm increment. This population, with a PPC range of 720-1598, was not observed in the 2 µm incremented chip most likely due insufficient pitch length, whereby this population may have ratcheted off the end of the chip.

In addition to LNCaP cells, ratcheting cytometry was also performed on PC3 cells to compare EpCAM expression profiles. Using a 2 µm incremented chip, differences in equilibrium pitches were observed between LNCaP cells and PC3 cells ratcheted at 5 Hz for about 10 minutes, in agreement with EpCAM expression levels (FIG. 14A). PC3s exhibited PPC signatures of 1-23 and 19-41 (p=0.01), which equilibrated at 14-20 µm and 22-26 µm pitches respectively. In characterizing cell separation behavior on both the 2 µm and 10 µm incremented chips it was determined that each chip design was optimal for different use cases. The 2 µm incremented chip was best used for precise surface marker analysis and separation within a single cell population or between populations with similar expression. The 10 µm incremented chip was best used in purifying a target cell population from heterogeneous cell solutions, such as blood, where the expression level of the target cells were significantly higher than the other populations.

The system was then assessed as a rare cell cytometer by spiking approximately 100 cancer cells into healthy blood, simulating prostate circulating tumor cell (CTCs) samples. The goal was to quantify surface expression profiles on CTCs but also address the major barrier of CTC purification which has limited MACS and other CTC capture systems. Low purity leads to difficulty in performing downstream molecular assays which can be dominated by signal from off-target cells. Using magnetic ratcheting cytometry, highly expressing CTCs can be quantitatively separated from the leukocyte background at high purity streamlining downstream precision assays. As a control, healthy blood was labeled with 1 µm αEpCAM particles and ratcheted through a 10 µm incremented chip to quantify contaminating leukocyte background. Most of non-specifically labeled leukocytes occupied a pitch range from 10-60 µm and equilibrated mostly at the 20 µm pitch corresponding to a PPC range of 1-25. From this data a "cut-off" pitch was set at 60 µm. Therefore, CTCs could be successfully purified as long as they equilibrated at a ≥70 µm pitch.

To simulate patient samples LNCaP (~100 cells/mL) were spiked into 1 mL volumes of whole blood from a healthy donor, diluted 5× in PBS, and then labeled with anti-EpCAM particles (labeled with 1 µm anti-EpCAM particles at $10^6$ particles/mL). The samples were incubated at room temperature for 2 hours with gentle agitation and stained with Hoescht to visualize cell nuclei. The entirety of the sample was then flowed or injected over the chip's loading patch (at 50 µL/min) while magnetized to pull the labeled cells onto the loading patch. After accumulation onto the loading patch, the cells were separated on a 10 µm incremented chip at 5 Hz and the entire chip was imaged under DAPI and FITC filter sets. Capture efficiency was determined by counting the number of FITC positive cells and comparing to a control. Purity characterization was performed similarly where ~2000 FITC labeled LNCaP cells were spiked into 1 mL of whole blood, labeled, then separated at 5 Hz. Purity was defined as the ratio of spiked LNCaP cells to the total number of cells binned by pitch.

Figure 15A:
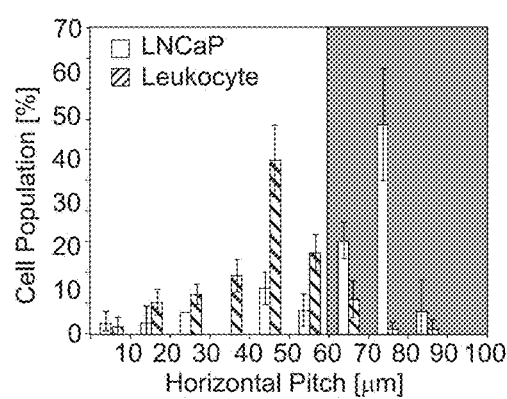
FIG. 15A illustrates the results of separating LNCaP cells from leukocytes as a function of pitch using a 10 µm incremented chip ratcheted at 5 Hz and setting a cut-off pitch at 60 µm. High purity separation of LNCaPs from leukocytes was achieved despite both populations shifting to higher pitches. The LNCaP majority equilibrated at the 70-100 µm pitches peaking at 80 µm while the leukocytes equilibrated between the 10-60 µm pitches peaking at 50 µm.
Figure 15B:
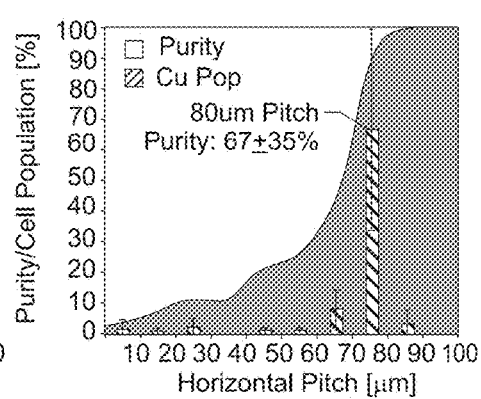
FIG. 15B illustrates a graph illustrating the purity, defined as the ratio of total number of LNCaPs to total cells, for each pitch was determined showing a maximum purity of 67±35% at the 80 µm pitch. The cumulative population (Cu Pop) of the spiked cells was determined by sequentially summing the spiked population beginning at the 10 µm pitch and showed 26% of the spiked population equilibrated below the cut-off pitch.

The spiked cells were successfully extracted from the leukocyte background and equilibrated mostly at the 80 µm pitch as seen in FIG. 15A. Of the spiked cells approximately 24.9±1.94% were purified on the ratcheting chip. This capture efficiency is comparable to MACS based techniques targeting prostate cancer cells with EpCAM. However, compared to standard MACS techniques the separation purity (FIG. 15B) was significantly higher, the max being 51%, where a majority of the LNCaPs were successfully extracted from the leukocyte background. Note that for traditional MACS any amount of magnetic labeling leads to capture, ultimately resulting in lower purity which ranges between 51% to 0.1%.

Interestingly, the spiked LNCaPs and non-specifically-labeled leukocytes occupied higher pillar pitches than observed in buffer. A majority of the LNCaPs, 74%, resided at the 80 µm pitch which was hypothesized as being attributed to an effective particle concentration increase due to the excluded volume of the red blood cells. Additionally, the non-specifically labeled leukocyte population demonstrated a shift towards the higher pitches but a vast majority, ~90%, remained at or below the cutoff pitch of 60 µm and therefore did not significantly affect the 70 µm-100 µm pitch purities. The system demonstrated minimal loss as shown in the cumulative distribution plots (FIG. 15B). 74% of the extracted LNCaPs were cleared past the cut-off pitch and highly purified. The purity of the extracted cells above an 80 µm pitch was 67±35% and contained 47±14% of the extracted population. In total, the ratcheting cytometry system was able to successfully concentrate and purify low concentrations of cancer cells from blood making it a tenable option as a clinical purification instrument for CTCs.

After validating the magnetic ratcheting cytometry system with spiked cancer cells, clinical blood samples of metastatic prostate cancer patients were run on the chip. It was expected that some prostate CTCs would exhibit high EpCAM expression (PPC 1700-3600) as observed in the spiking experiments, thereby equilibrating past the cutoff pitch under a 5 Hz ratchet. Of note, suspected prostate CTCs were defined as large nucleated cells (diameter ≥9 µm) with high EpCAM expression (PPC≥1700) and no detectable CD45 expression as quantified by florescence. Three patient samples were stained and labeled (stained with Hoechst & CD 45, diluted 5× in PBS and labeled with particles) and separated on the chip. Cells were separated using 5 Hz ratcheting and imaged under DAPI and TRITC filter sets.

Figure 16:
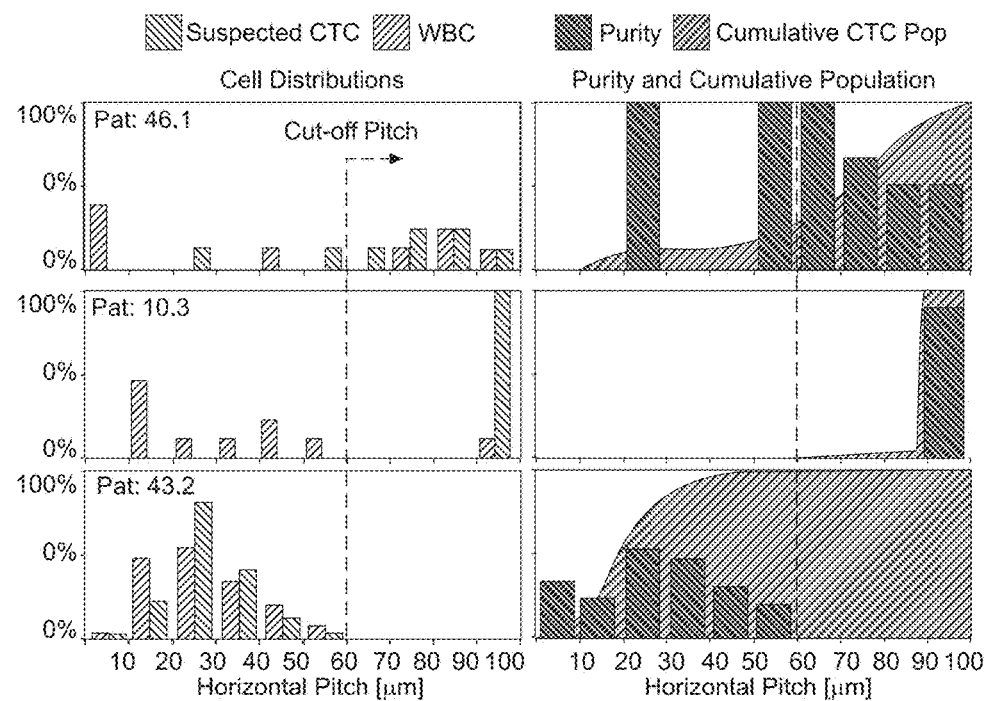
FIG. 16 illustrates blood biopsy results (1 mL volume) from three patients with metastatic castration resistant cancer. Cells in blood were magnetically labeled with 1 µm αEpCAM particles and cells were separated on a 10 µm incremented chip ratcheted at 5 Hz. Cell distributions and purity are illustrated. Patients 46.1 and 10.3 had several cells (N=7 and N=8 CTCs respectively) which equilibrated between the 70-100 µm pitches with purity ranging from 50% to 100%. In contrast, patient 43.2 exhibited no cells in the 70-100 µm pitches and a skewed cumulative population towards the lower pitches.

Two patients of which had several large, CD45 negative cells which equilibrated at the 70-100 µm pitches as seen in FIG. 16. These results were similar to the spiking experiments and, upon observation, demonstrated morphological characteristics consistent with CTC profiles including large nuclear to cytoplasmic ratio or multinucleated cells. The CTC separation purity was high, where each binned purity for the 70-100 µm pitches ranged between 50% to 100% for these two patients (FIG. 16; patients 46.1 and 10.3). Furthermore, the loss of suspicious cells was low as the cumulative populations of suspected prostate CTCs for these patients exhibited a skew towards the 70-100 µm pitch values. Between 78% and 100% of the suspected CTCs were above the cut-off pitch for the two patients respectively, demonstrating high purity separation without significant loss of the captured cells. Overall, the ratcheting cytometry system isolated EpCAM expressing suspected prostate CTCs from peripheral whole blood with an average purity of ~74%, a substantial improvement over traditional MACS-based techniques. The system shows promise as a high efficiency extraction method where high purity is also necessary, such as is the case for downstream sequencing for precision medicine.

Magnetic ratcheting cytometry enables widely used magnetic labeling techniques to be deployed for robust, efficient, and quantitative separations, while simultaneously concentrating target cells. Any magnetic particle that is used for MACS based separations, and even other smaller particles can also be used in the described invention. For example specialized magnetic nanoparticles or microparticles with fluorescent dyes, magnetic quantum dots, plasmonic particles with magnetic cores, magnetic particles with surface-labile groups which allow for subsequent removal of the particles from the cells, etc. may be used. Using 1:1 aspect ratio permalloy micro-pillar arrays the magnetophoretic force envelope has been increased some 10-fold compared to thin film ratcheting systems. Increased force not only decreases processing time but enables the use of small particles which is advantageous due to their increased labeling efficiency attributed to large diffusion lengths, and the ability to have a larger number of quantized labeling levels compared to larger particles. In developing a theoretical framework for high force magnetic ratcheting, arrays with gradient pitch can be rationally designed and constructed to achieve separation and concentration of magnetic particles and cells. Furthermore, these gradient pitch arrays achieve separation in a temporally stable, equilibrium based manner making them more robust than kinetic or flow based separation techniques which are sensitive to dynamic physical parameters such as flow rate. Additionally, magnetic ratcheting cytometry cleanly integrates separation and quantification (on the gradient pillar slide) into a single step assay, bringing a much needed quantitative aspect to MACS systems.

As demonstrated, ratcheting cytometry is an effective tool to capture and quantitatively separate rare cell types in both laboratory and clinical settings. Particularly, the system addresses the major challenge of purity that has plagued traditional MACS based systems. Separation resolution can be increased by using smaller magnetic particles to reduce the effective iron content per particle which will likely increase sample purity by reducing labeling time and off-target labeling. Another improvement includes a combined 10 µm and 2 µm incremented chip to enable both high dynamic range and high resolution separation. First cell populations can undergo a coarse separation in one axis and a fine separation in an orthogonal axis (see array of FIG. 6C), thereby accommodating samples with a large PPC range without sacrificing separation resolution.

Another use is to concentrate the separated cell populations by ratcheting orthogonally relative to initial ratcheting direction for the array to collect the cells at the bottom of each pitch zone. For example, the chip illustrated in FIGS. 4A-4D can be used in this manner. In this way, the concentrated cells could be extracted from the chip via fluid access wells aligned with the bottom of each pitch zone. Another option is to integrate all required analysis into the chip where cells, once separated, can be manipulated at high resolution into different modules directly on chip. Indeed, ratcheting cytometry is not limited solely to separation but can be used as a manipulation platform to develop fully integrated lab-on-a chip systems enabling assays to be performed from whole samples down to single cells directly on the same chip. For example, target cells can first be quantitatively separated and concentrated using the gradient pitch arrays and then manipulated through fluid reservoirs to perform wash steps or various biochemical assays, or arrayed to enable single-cell interrogation. The ratcheting system described herein is a new platform for lab-on-a-chip automation, enabling sample-to-answer assays to be performed rapidly with single cell resolution.

While embodiments of the present invention have been shown and described, various modifications may be made without departing from the scope of the present invention. In addition, while various dimensions have been described and illustrated in the drawings it should be understood that these are exemplary and are not limiting as variations are included within the scope of the invention. Similarly, while the rotating magnetic wheel has been described in the context of many embodiments, other ways of generating a rotating or oscillation magnetic field can be used as is disclosed herein. The invention, therefore, should not be limited except to the following claims and their equivalents.

What is claimed is:

1. A system for the magnetic separation of magnetic objects comprising:
    a substrate;
    an array of ferromagnetic elements disposed on the substrate in rows and columns, wherein the array comprises a plurality of pitch zones having increased pitch between adjacent rows or columns of ferromagnetic elements;
    a support surface disposed over the array of ferromagnetic elements and configured to receive the particles or cells; and
    a rotating magnetic wheel disposed adjacent to the support surface, the rotating magnetic wheel having disposed therein a plurality of permanent magnets arranged in a partial halbach array.

2. The system of claim 1, wherein the periodic array of ferromagnetic elements comprise $Ni_xFe_y$.

3. The system of claim 1, wherein the rotating magnetic wheel is configured to twist in a plane that is substantially parallel to the support surface.

4. The system of claim 1, wherein the plurality of pitch zones have increased pitch in a direction along the rows or columns of the array.

5. The system of claim 1, wherein the increased pitch is linear and within the range of about 1 μm to about 10 μm.

6. The system of claim 1, further comprising a top disposed above the support surface and containing an input well leading to a channel disposed above the array of ferromagnetic elements.

7. The system of claim 6, wherein the top further comprises a plurality of output wells disposed adjacent to the array of ferromagnetic elements, wherein the output wells are located at ends of rows or columns of ferromagnetic elements.

8. The system of claim 1, further comprising a housing holding the rotating magnetic wheel, the housing having a support plate disposed therein and a rotatable ring disposed on the support plate and rotatable relative thereto, the rotatable ring secured to a first motor mechanically coupled to the magnetic wheel through a first drive train, wherein the housing contains a second motor mechanically coupled to a gear via a second drive train, the gear interfacing with the rotatable ring.

9. The system of claim 8, further comprising a manipulator operably coupled to one or both of the first motor and the second motor, the manipulator configured to twist the magnetic wheel in a plane that is substantially parallel to the support surface in response to a command.

10. The system of claim 1, wherein the substrate is flexible.

* * * * *